(12) United States Patent
Fleming et al.

(10) Patent No.: US 9,908,846 B2
(45) Date of Patent: Mar. 6, 2018

(54) COMPOSITION, SYNTHESIS, AND USE OF NEW ARYLSULFONYL ISONITRILES

(71) Applicant: DUQUESNE UNIVERSITY OF THE HOLY GHOST, Pittsburgh, PA (US)

(72) Inventors: Fraser Fergusson Fleming, Falls Church, VA (US); Jesus Armando Lujan-Montelongo, Tlalnepantla de Baz (MX)

(73) Assignee: Duquesne University of the Holy Spirit, Pittsburgh, PA (US)

(*) Notice: Subject to any disclaimer, the term of this patent is extended or adjusted under 35 U.S.C. 154(b) by 0 days.

(21) Appl. No.: 14/626,984

(22) Filed: Feb. 20, 2015

(65) Prior Publication Data

US 2015/0239833 A1    Aug. 27, 2015

Related U.S. Application Data

(60) Provisional application No. 61/942,850, filed on Feb. 21, 2014.

(51) Int. Cl.
| | | |
|---|---|---|
| *C07C 317/28* | (2006.01) | |
| *C07C 303/36* | (2006.01) | |
| *C07C 315/00* | (2006.01) | |
| *C07C 317/30* | (2006.01) | |

(52) U.S. Cl.
CPC .......... *C07C 317/28* (2013.01); *C07C 317/30* (2013.01); *C07C 2101/14* (2013.01)

(58) Field of Classification Search
None
See application file for complete search history.

(56) References Cited

U.S. PATENT DOCUMENTS

| | | | | |
|---|---|---|---|---|
| 5,258,526 A | * | 11/1993 | Knuppel | C07D 207/34 548/526 |
| 8,269,032 B1 | | 9/2012 | Fleming et al. | |
| 8,563,763 B2 | | 10/2013 | Fleming et al. | |
| 2012/0053180 A1 | | 3/2012 | Kang et al. | |
| 2012/0259137 A1 | | 10/2012 | Fleming et al. | |
| 2013/0203738 A1 | | 8/2013 | Nishimura et al. | |

FOREIGN PATENT DOCUMENTS

WO    2013/174947 A1    11/2013

OTHER PUBLICATIONS

Chemical Abstract Registry No. 1155116-55-4, indexed in the Registry File on STN CAS Online Jun. 10, 2009.*
Chemical Abstract Registry No. 207853-59-6, indexed in the Registry File on STN CAS Online Jul. 1, 1998.*
Chemical Abstract Registry No. 1249611-67-3, indexed in the Registry File on STN CAS Online Oct. 31, 2010.*
Chemical Abstract Registry No. 1154878-91-7, indexed in the Registry File on STN CAS Online Jun. 10, 2009.*
Chemical Abstract Registry No. 1281594-92-0, indexed in the Registry File on STN CAS Online Apr. 17, 2011.*
Kim et al., Synthesis and biological evaluation of triazolothienopyrimidine derivatives as novel HIV-1 replication inhibitors. Bioorganic & Medicinal Chemistry Letters, 2013, 23, 153-157.*
Schobert et al., 4-(3-Halo/amino-4,5-dimethoxyphenyl)-5-aryloxazoles and -N-methylimidazoles That are Cytotoxic against Combretastatin A Resistant Tumor Cells and Vascular Disrupting in a Cisplatin Resistant Germ Cell Tumor Model. Journal of Medicinal Chemistry, 2010, 53, 6595-6602.*
Tsui et al., Rhodium(I)-Catalyzed Addition of Arylboronic Acids to (Benzyl-/Arylsulfonyl)acetonitriles: Efficient Synthesis of (Z)-β-Sulfonylvinylamines and β-Keto Sulfones. Organic Letters, 2011, 13, 208-211.*
Chemical Abstract Registry No. 1153968-16-1, indexed in the Registry File filed on STN CAS Online Jun. 8, 2009.*
Leusen, D. V. and Leusen, A. M. V. 2004. Synthetic Uses of Tosylmethyl Isocyanide (TosMIC). Organic Reactions. 57:3:417-666.*
Notification of Transmittal of the International Search Report and the Written Opinion of the International Searching Authority, or the Declaration, dated May 20, 2015.

* cited by examiner

*Primary Examiner* — Michael Barker
*Assistant Examiner* — Po-Chih Chen
(74) *Attorney, Agent, or Firm* — Eckert Seamans Cherin & Mellott, LLC; Carol A. Marmo

(57) ABSTRACT

This invention relates to novel isonitriles, including arylsulfonyl isonitriles, and methods for their synthesis. The isonitriles include a conjugated ring system. The structure is designed with the flexibility to have multiple substitution patterns. The isonitriles may be used in applications including, but not limited to, pharmaceutical compositions.

3 Claims, 22 Drawing Sheets

COMPOSITION, SYNTHESIS, AND USE OF NEW ARYLSULFONYL ISONITRILES

CROSS-REFERENCE TO RELATED APPLICATIONS

This application claims priority under 35 U.S.C. § 119(e) to U.S. Provisional Patent Application Ser. No, 61/942,850, filed Feb. 21, 2014, entitled "Composition, Synthesis, and Use of a New Class of Isonitriles", which is herein incorporated by reference.

GOVERNMENTAL INTEREST

This invention was made with Government support under grant AI051352-04 awarded by the National Institutes of Health. The government has certain rights in the invention.

FIELD OF THE INVENTION

The invention relates to arysulfonyl isonitrile compounds and their synthesis. The invention also relates to new arylsulfonyl isonitriles as intelinediates for synthesizing isonitriles and nitriles.

BACKGROUND OF THE INVENTION

Isonitrile compounds and derivatives thereof are known in the art and can be used in various applications, including the fields of medicine and pharmaceuticals. For example, bioactive isonitrile-containing metabolites may be isolated and used to treat widespread infections and deaths caused by malaria, The spread of resistant strains and the rise in global temperatures has made the treatment of malaria one of the highest priorities of the World Health Organization for the third world and North America Various methods for synthesizing isonitrile compounds are also known in the art. For example, it is known that isonitriles can be synthesized by the reaction of primary amines with dichiorocarbene Or by dehydration of a formamide with phosphorus oxychloride. The Hofmann synthesis is a chemical test for primary amines based on their reaction with potassium hydroxide and chloroform as dichlorocarhene precursors to isonitriles. Another route to producing isonitriles is by reaction of organolithium compounds with oxazoles and benzoxazoles. A further synthetic route toward isonitriles includes condensation of an amine with formic acid to yield a formamide, and subsequent dehydration of this formamide. Phosgene can be used in combination with the formamide to yield isonitriles.

Isonitriles are used as reactants in multi-component Ugi and Passerini condensations, heterocycle synthesis, in radical and Pauson-Khand reactions and as ligands and in medical imaging.

There are disadvantages associated with the known methods of synthesizing isonitriles. The deprotonation-alkylation syntheses are limited to special substrates and conjugate additions with alkylisonitriles are rare, extremely challenging, and require additional activation through further conjugation. There are little or no known methodologies that provide direct, rapid access to bioactive isonitrile-containing carbocycles. Multi-step sequences are often required. For example, the synthesis of an anti-fouling isonitrile may require as many as ten steps to convert a ketone into an isonitrile.

The commercial availability of isonitriles is limited and those that are commercially available can be expensive.

Thus, there is a need in the art to develop new connectivity methods, as well as, isonitriles having new structural diversity and fundamental reactivity patterns in alkylations and conjugate additions. Furthermore, it would be advantageous for the new methodologies of preparing isonitriles to include a minimum number of steps which are cost effective to perform and that result in high yields.

SUMMARY OF THE INVENTION

The invention relates in general to novel isonitrile compounds and, in particular, to novel arylsulfonyl isonitrile compounds. Further, the invention includes synthesis of the novel arylsulfonyl isonitrile compounds and their use as precursors or building blocks for preparing other isonitrile compounds.

One aspect of the invention provides a compound represented by a general structure of Formula I:

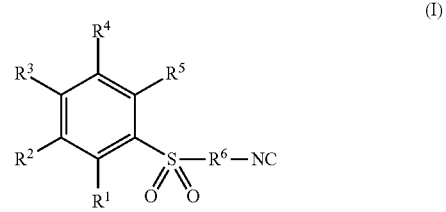

(I)

wherein, $R^1$, $R^2$, $R^3$, $R^4$ and $R^5$ are the same or different and each is selected from hydrogen, alkyl, halogen, haloalkyl and O—X wherein X is selected from alkyl and aryl, and $R^6$ is selected from alkyl and cyclic or polycyclic, aromatic or non-aromatic, structure, e.g., one or more rings, such as, but not limited to a cyclic six-membered ring.

In certain embodiments, $R^1$, $R^2$, $R^3$, $R^4$ and $R^5$ are the same or different and each is selected from hydrogen, C1-C6 alkyl, halogen, C1-C6 haloalkyl and O—X wherein X is selected from $C_1$-$C_6$ alkyl and aryl, and $R^6$ is selected from $C_1$-$C_6$ alkyl and cyclic or polycyclic, aromatic or non-aromatic, structure, e.g., one or more rings, such as, but not limited to a cyclic six-membered ring.

Further, in certain embodiments, $R^1$, $R^2$, $R^3$, $R^4$ and $R^5$ are the same or different and each is selected from hydrogen, $C_1$-$C_4$ alkyl, halogen, $C_1$-$C_4$ haloalkyl and O—X wherein X is selected from $C_1$-$C_4$ alkyl and aryl, and $R^6$ is selected from $C_1$-$C_4$ alkyl and cyclic or polycyclic, aromatic or non-aromatic, structure, e.g., one or more rings, such as, but not limited to a cyclic six-membered ring.

Furthermore, in certain embodiments, two of $R^1$, $R^2$, $R^3$, $R^4$ and $R^5$, such as, but not limited to $R^1$ and $R^2$ or $R^2$ and $R^3$, can come together to form a benzo ring.

In certain embodiments, X is phenyl.

In certain embodiments, $R^6$ is $CH_2$.

In certain embodiments, halogen is selected from fluoride and chloride.

In certain embodiments, the haloalkyl is $CF_3$.

In certain embodiments, one of $R^1$, $R^2$, $R^3$, $R^4$ and $R^5$ is $C_1$-$C_4$ alkyl, halogen, $C_1$-$C_4$ haloalkyl or O—X and the remaining R substituents are the same and each is hydrogen.

In certain embodiments, $R^1$, $R^2$, $R^4$ and $R^5$ are the same and each is hydrogen, and $R^3$ is $C_1$-$C_4$ alkyl or halogen.

In certain embodiments, $R^1$, $R^2$, $R^3$ and $R^4$ are the same and each is hydrogen, and $R^5$ is $C_1$-$C_4$ alkyl or O—X.

In certain embodiments, two of $R^1$, $R^2$, $R^3$, $R^4$ and $R^5$ are the same or different and each is $C_1$-$C_4$ alkyl, halogen, $C_1$-$C_4$ haloalkyl or O—X and the remaining R substituents are each hydrogen.

In certain embodiments, two of $R^1$, $R^2$, $R^3$, $R^4$ and $R^5$ are the same and each is $C_1$-$C_4$ alkyl, halogen, $C_1$-$C_4$ haloalkyl or O—X and the remaining R substituents are the same and each is hydrogen.

In certain embodiments, $R^1$, $R^3$ and $R^5$ are the same and each is hydrogen and, $R^2$ and $R^4$ are the same and each is halogen or O—X.

In certain embodiments, the compound of the invention is represented by a general structure of Formula II:

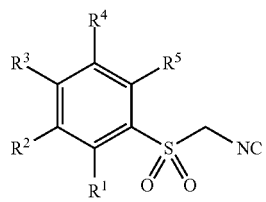

(II)

wherein, $R^1$, $R^2$, $R^3$, $R^4$ and $R^5$ are the same or different and each is selected from hydrogen, alkyl, halogen, haloalkyl and O—X wherein X is selected from alkyl and aryl.

In certain embodiments, $R^1$, $R^2$, $R^3$, $R^4$ and $R^5$ are the same or different and each is selected from hydrogen, $C_1$-$C_6$ alkyl, halogen, $C_1$-$C_6$ haloalkyl and O—X wherein X is selected from $C_1$-$C_6$ alkyl and aryl.

Further, in certain embodiments, $R^1$, $R^2$, $R^3$, $R^4$ and $R^5$ are the same or different and each is selected from hydrogen, $C_1$-$C_4$ alkyl, halogen, $C_1$-$C_4$ haloalkyl and O—X wherein X is selected from $C_1$-$C_4$ alkyl and aryl.

Furthermore, in certain embodiments, two of $R^1$, $R^2$, $R^3$, $R^4$ and $R^5$, such as, but not limited to $R^1$ and $R^2$ or $R^2$ and $R^3$, can come together to form a benzo ring.

In certain embodiments, X is phenyl.

In certain embodiments, halogen is selected from fluoride and chloride.

In certain embodiments, the haloalkyl is $CF_3$.

In certain embodiments, one of $R^1$, $R^2$, $R^3$, $R^4$ and $R^5$ is $C_1$-$C_4$ alkyl, halogen, $C_1$-$C_4$ haloalkyl or O—X and the remaining R substituents are the same and each is hydrogen.

In certain embodiments, $R^1$, $R^2$, $R^4$ and $R^5$ are the same and each is hydrogen, and $R^3$ is $C_1$-$C_4$ alkyl or halogen.

In certain embodiments, $R^1$, $R^2$, $R^3$ and $R^4$ are the same and each is hydrogen, and $R^3$ is $C_1$-$C_4$ alkyl or O—X.

In certain embodiments, two of $R^1$, $R^2$, $R^3$, $R^4$ and $R^5$ are the same or different and each is $C_1$-$C_4$ alkyl, halogen, $C_1$-$C_4$ haloalkyl or O—X and the remaining R substituents are each hydrogen.

In certain embodiments, two of $R^1$, $R^2$, $R^3$, $R^4$ and $R^5$ are the same and each is $C_1$-$C_4$ alkyl, halogen, $C_1$-$C_4$ haloalkyl or O—X and the remaining R substituents are the same and each is hydrogen.

In certain embodiments, $R^1$, $R^3$ and $R^5$ are the same and each is hydrogen and, $R^2$ and $R^4$ are the same and each is halogen or O—X.

In certain other embodiments, the invention provides a compound represented by a general structure of Formula III:

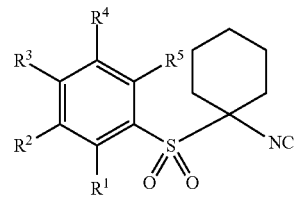

(III)

wherein, $R^1$, $R^2$, $R^3$, $R^4$ and $R^5$ are the same or different and each is selected from hydrogen, alkyl, halogen, haloalkyl and O—X wherein X is selected from alkyl and aryl.

In certain embodiments, $R^1$, $R^2$, $R^3$, $R^4$ and $R^5$ are the same or different and each is selected from hydrogen, $C_1$-$C_6$ alkyl, halogen, $C_1$-$C_6$ haloalkyl and O—X wherein X is selected from $C_1$-$C_6$ alkyl and aryl.

Further, in certain embodiments, $R^1$, $R^2$, $R^3$, $R^4$ and $R^5$ are the same or different and each is selected from hydrogen, $C_1$-$C_4$ alkyl, halogen, $C_1$-$C_4$ haloalkyl and O—X wherein X is selected from $C_1$-$C_4$ alkyl and aryl.

Furthermore, in certain embodiments, two of $R^1$, $R^2$, $R^3$, $R^4$ and $R^5$, such as, but not limited to $R^1$ and $R^2$ or $R^2$ and $R^3$, can come together to form a benzo ring.

In certain embodiments, X is phenyl.

In certain embodiments, halogen is selected from fluoride and chloride.

In certain embodiments, the haloalkyl is $CF_3$.

In certain embodiments, one of $R^1$, $R^2$, $R^3$, $R^4$ and $R^5$ is $C_1$-$C_4$ alkyl, halogen, $C_1$-$C_4$ haloalkyl or O—X and the remaining R substituents are the same and each is hydrogen.

In certain embodiments, $R^1$, $R^2$, $R^4$ and $R^5$ are the same and each is hydrogen, and $R^3$ is $C_1$-$C_4$ alkyl or halogen.

In certain embodiments, $R^1$, $R^2$, $R^3$ and $R^4$ are the same and each is hydrogen, and $R^5$ is $C_1$-$C_4$ alkyl or O—X.

In certain embodiments, two of $R^1$, $R^2$, $R^3$, $R^4$ and $R^5$ are the same or different and each is $C_1$-$C_4$ alkyl, halogen, $C_1$-$C_4$ haloalkyl or O—X and the remaining R substituents are each hydrogen.

In certain embodiments, two of $R^1$, $R^2$, $R^3$, $R^4$ and $R^5$ are the same and each is $C_1$-$C_4$ alkyl, halogen, $C_1$-$C_4$ haloalkyl or O—X and the remaining R substituents are the same and each is hydrogen.

In certain embodiments, $R^1$, $R^3$ and $R^5$ are the same and each is hydrogen and, $R^2$ and $R^4$ are the same and each is halogen or O—X.

In certain other embodiments, the invention provides a compound represented by a general structure of Formula IV:

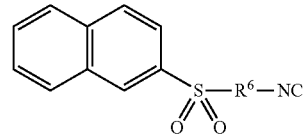

(IV)

wherein $R^6$ is as defined for Formula I.

Another aspect of the invention provides a method of preparing the compound represented by the general structure of Formula I. The method includes reacting an arylsulfonate with formamide to form an intermediate formamide-containing product; and dehydrating the intermediate formamide-containing product to form the arylsulfonyl isonitrile.

BRIEF DESCRIPTION OF THE DRAWINGS

The various embodiments of the invention will be better understood when read with reference to the following figures.

DETAILED DESCRIPTION OF THE INVENTION

Figure 1:
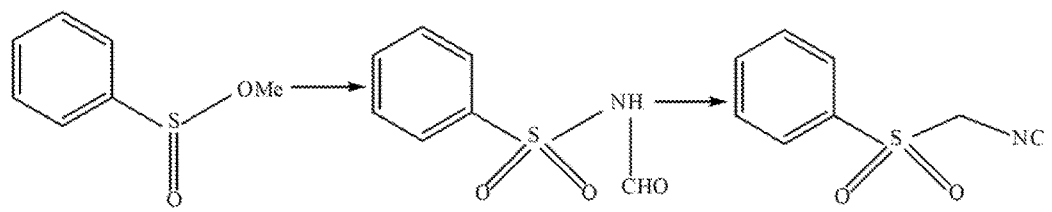
FIG. 1 illustrates a condensation/dehydration reaction scheme for synthesis of an arylsulfonyl isonitrile, in accordance with certain embodiments of the invention.

The invention relates in general to novel isonitrile compounds and, in particular, to new arylsulfonyl isonitriles that may be synthesized from readily available materials. The structures of the arylsulfonyl isonitriles are designed with the flexibility to have multiple substitution patterns.

Other than the operating examples, or where otherwise indicated, all numbers expressing quantities of ingredients, processing conditions and the like used in the specification and claims are to be understood as being modified in all instances by the term "about". Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical values, however, may contain certain errors, such as, for example, equipment and/or operator error, necessarily resulting from the standard deviation found in their respective testing measurements.

Also, it should be understood that any numerical range recited herein is intended to include all sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value of less than or equal to 10.

Any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between the incorporated material and the existing disclosure material.

The present disclosure describes several different features and aspects of the invention with reference to various exemplary non-limiting embodiments. It is understood, however, that the invention embraces numerous alternative embodiments, which may be accomplished by combining any of the different features, aspects, and embodiments described herein in any combination that one of ordinary skill in the art would find useful.

The new arylsulfonyl isonitrile compounds of the present invention have the general formula I:

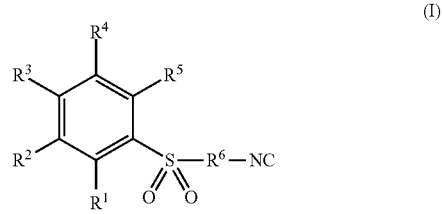

(I)

wherein, $R^1$, $R^2$, $R^3$, $R^4$ and $R^5$ are the same or different and each is selected from hydrogen, alkyl, halogen, haloalkyl and O—X wherein X is selected from alkyl and aryl, and $R^6$ is selected from alkyl and cyclic or polycyclic, aromatic or non-aromatic, structure, e.g., one or more rings, such as, but not limited to a cyclic six-membered ring.

In certain embodiments, $R^1$, $R^2$, $R^3$, $R^4$ and $R^5$ are the same or different and each is selected from hydrogen, $C_1$-$C_6$ alkyl, halogen, $C_1$-$C_6$ haloalkyl and O—X wherein X is selected from $C_1$-$C_6$ alkyl and aryl, and $R^6$ is selected from $C_1$-$C_6$ alkyl and cyclic or polycyclic, aromatic or non-aromatic, structure, e.g., one or more rings, such as, but not limited to a cyclic six-membered ring.

Further, in certain embodiments, $R^1$, $R^2$, $R^3$, $R^4$ and $R^5$ are the same or different and each is selected from hydrogen, $C_1$-$C_4$ alkyl, halogen, $C_1$-$C_4$ haloalkyl and O—X wherein X is selected from $C_1$-$C_4$ alkyl and aryl, and $R^6$ is selected from $C_1$-$C_4$ alkyl and cyclic or polycyclic, aromatic or non-aromatic, structure, e.g., one or more rings, such as, but not limited to a cyclic six-membered ring.

Furthermore, in certain embodiments, two of $R^1$, $R^2$, $R^3$, $R^4$ and $R^5$, such as, but not limited to $R^1$ and $R^2$ or $R^2$ and $R^3$, can come together to form a benzo ring.

In certain embodiments, X is phenyl.

In certain embodiments, $R^6$ is $CH_2$.

In certain embodiments, halogen is selected from fluoride and chloride.

In certain embodiments, the haloalkyl is $CF_3$.

In certain embodiments, one of $R^1$, $R^2$, $R^3$, $R^4$ and $R^5$ is $C_1$-$C_4$ alkyl, halogen, $C_1$-$C_4$ haloalkyl or O—X and the remaining R substituents are the same and each is hydrogen.

In certain embodiments, $R^1$, $R^2$, $R^4$ and $R^5$ are the same and each is hydrogen, and $R^3$ is $C_1$-$C_4$ alkyl or halogen.

In certain embodiments, $R^1$, $R^2$, $R^3$ and $R^4$ are the same and each is hydrogen, and $R^5$ is $C_1$-$C_4$ alkyl or O—X.

In certain embodiments, two of $R^1$, $R^2$, $R^3$, $R^4$ and $R^5$ are the same or different and each is $C_1$-$C_4$ alkyl, halogen, $C_1$-$C_4$ haloalkyl or O—X and the remaining R substituents are each hydrogen.

In certain embodiments, two of $R^1$, $R^2$, $R^3$, $R^4$ and $R^5$ are the same and each is $C_1$-$C_4$ alkyl, halogen, $C_1$-$C_4$ haloalkyl or O—X and the remaining R substituents are the same and each is hydrogen.

In certain embodiments, $R^1$, $R^3$ and $R^5$ are the same and each is hydrogen and, $R^2$ and $R^4$ are the same and each is halogen or O—X.

In certain embodiments, the new arylsulfonyl isonitrile compounds of the present invention have the general formula II:

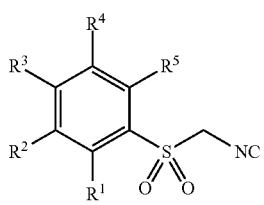

(II)

wherein, $R^1$, $R^2$, $R^3$, $R^4$ and $R^5$ are the same or different and each is selected from hydrogen, alkyl, halogen, haloalkyl and O—X wherein X is selected from alkyl and aryl.

In certain embodiments, $R^1$, $R^2$, $R^3$, $R^4$ and $R^5$ are the same or different and each is selected from hydrogen, $C_1$-$C_6$ alkyl, halogen, $C_1$-$C_6$ haloalkyl and O—X wherein X is selected from $C_1$-$C_6$ alkyl and aryl.

Further, in certain embodiments, $R^1$, $R^2$, $R^3$, $R^4$ and $R^5$ are the same or different and each is selected from hydrogen, $C_1$-$C_4$ alkyl, halogen, $C_1$-$C_4$ haloalkyl and O—X wherein X is selected from $C_1$-$C_4$ alkyl and aryl.

Furthermore, in certain embodiments, two of $R^1$, $R^2$, $R^3$, $R^4$ and $R^5$, such as, but not limited to $R^1$ and $R^2$ or $R^2$ and $R^3$, can come together to form a benzo ring.

In certain embodiments, X is phenyl.

In certain embodiments, halogen is selected from fluoride and chloride.

In certain embodiments, the haloalkyl is $CF_3$.

In certain embodiments, one of $R^1$, $R^2$, $R^3$, $R^4$ and $R^5$ is $C_1$-$C_4$ alkyl, halogen, $C_1$-$C_4$ haloalkyl or O—X and the remaining R substituents are the same and each is hydrogen.

In certain embodiments, $R^1$, $R^2$, $R^4$ and $R^5$ are the same and each is hydrogen, and $R^3$ is $C_1$-$C_4$ alkyl or halogen.

In certain embodiments, $R^1$, $R^2$, $R^3$ and $R^4$ are the same and each is hydrogen, and $R^5$ is $C_1$-$C_4$ alkyl or O—X.

In certain embodiments, two of $R^1$, $R^2$, $R^3$, $R^4$ and $R^5$ are the same or different and each is $C_1$-$C_4$ alkyl, halogen, $C_1$-$C_4$ haloalkyl or O—X and the remaining R substituents are each hydrogen.

In certain embodiments, two of $R^1$, $R^2$, $R^3$, $R^4$ and $R^5$ are the same and each is $C_1$-$C_4$ alkyl, halogen, $C_1$-$C_4$ haloalkyl or O—X and the remaining R substituents are the same and each is hydrogen.

In certain embodiments, $R^1$, $R^3$ and $R^5$ are the same and each is hydrogen and, $R^2$ and $R^4$ are the same and each is halogen or O—X.

In certain other embodiments, the new arylsulfonyl isonitrile compounds of the present invention have the general formula III:

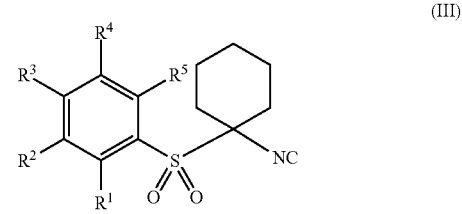

(III)

wherein, $R^1$, $R^2$, $R^3$, $R^4$ and $R^5$ are the same or different and each is selected from hydrogen, alkyl, halogen, haloalkyl and O—X wherein X is selected from alkyl and aryl.

In certain embodiments, $R^1$, $R^2$, $R^3$, $R^4$ and $R^5$ are the same or different and each is selected from hydrogen, $C_1$-$C_6$ alkyl, halogen, $C_1$-$C_6$ haloalkyl and O—X wherein X is selected from $C_1$-$C_6$ alkyl and aryl.

Further, in certain embodiments, $R^1$, $R^2$, $R^3$, $R^4$ and $R^5$ are the same or different and each is selected from hydrogen, $C_1$-$C_4$ alkyl, halogen, $C_1$-$C_4$ haloalkyl and O—X wherein X is selected from $C_1$-$C_4$ alkyl and aryl.

Furthermore, in certain embodiments, two of $R^1$, $R^2$, $R^3$, $R^4$ and $R^5$, such as, but not limited to $R^1$ and $R^2$ or $R^2$ and $R^3$, can come together to form a benzo ring.

In certain embodiments, X is phenyl.

In certain embodiments, halogen is selected from fluoride and chloride.

In certain embodiments, the haloalkyl is $CF_3$.

In certain embodiments, one of $R^1$, $R^2$, $R^3$, $R^4$ and $R^5$ is $C_1$-$C_4$ alkyl, halogen, $C_1$-$C_4$ haloalkyl or O—X and the remaining R substituents are the same and each is hydrogen.

In certain embodiments, $R^1$, $R^2$, $R^4$ and $R^5$ are the same and each is hydrogen, and $R^3$ is $C_1$-$C_4$ alkyl or halogen.

In certain embodiments, $R^1$, $R^2$, $R^3$ and $R^4$ are the same and each is hydrogen, and $R^5$ is $C_1$-$C_4$ alkyl or O—X.

In certain embodiments, two of $R^1$, $R^2$, $R^3$, $R^4$ and $R^5$ are the same or different and each is $C_1$-$C_4$ alkyl, halogen, $C_1$-$C_4$ haloalkyl or O—X and the remaining R substituents are each hydrogen.

In certain embodiments, two of $R^1$, $R^2$, $R^3$, $R^4$ and $R^5$ are the same and each is $C_1$-$C_4$ alkyl, halogen, $C_1$-$C_4$ haloalkyl or O—X and the remaining R substituents are the same and each is hydrogen.

In certain embodiments, $R^1$, $R^3$ and $R^5$ are the same and each is hydrogen and, $R^2$ and $R^4$ are the same and each is halogen or O—X.

For example, $R^1$, $R^2$, $R^3$, $R^4$ and $R^5$ can include the following combinations.

| $R^1$ | $R^2$ | $R^3$ | $R^4$ | $R^5$ |
|---|---|---|---|---|
| H | H | H | H | H |
| H | H | $CH_3$ | H | H |
| H | H | H | H | $CH_3$ |
| H | H | F | H | H |
| H | H | Cl | H | H |
| H | H | $CF_3$ | H | H |
| H | Cl | H | Cl | H |
| H | H | H | H | $OCH_3$ |
| H | H | H | H | OPh |
| H | H | $OCH_3$ | $OCH_3$ | H |
| $OCH_3$ | H | H | H | $OCH_3$ |
| $OCH_3$ | H | H | $CF_3$ | H |
| $CH_3$ | H | H | H | H |
| H | H | $CH_3$ | H | H |

In certain other embodiments, the new arylsulfonyl isonitrile compounds of the present invention have the general formula IV:

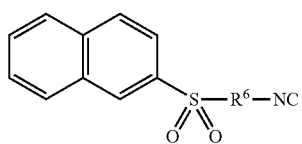

(IV)

wherein $R^6$ is as defined for Formula I.

The compounds of the invention may be readily synthesized using organic chemistry techniques. The syntheses of various embodiments of the isonitrile precursors and products are described herein. It should be noted that the featured embodiments are intended to be exemplary and are in no way limiting to the scope of the isonitrile precursors and products as described herein. For example, the compounds of Formulas I and II can be prepared according to certain embodiments of the invention. In general, condensation and dehydration reactions may be conducted to form the compounds of Formulas I and II. These compounds then may be used as precursors or building blocks to form other arylsulfonyl isonitriles. In certain embodiments, compounds represented by Formula I and Formula II can be subjected to double alkylation reactions to form the arylsulfonyl isonitrile represented by Formula III. Further, the compounds of Formulas III and IV may be used as precursors or building blocks to form other isonitrile compounds, such as by exchange reactions.

Figure 2:
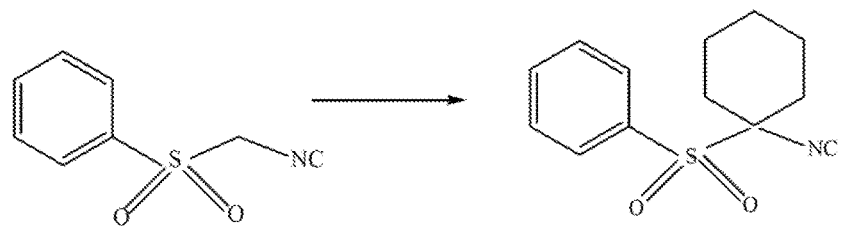
FIG. 2 illustrates a double alkylation reaction scheme for synthesis of an arylsulfonyl isonitrile, in accordance with certain embodiments of the invention.

Certain specific synthesis examples are discussed in detail in FIGS. 1 and 2.

FIG. 1 shows a reaction scheme for preparing arylsulfonyl isonitrile of Formula II, in accordance with certain embodiments of the invention. Compounds represented by the general structure of Formula II herein can be prepared by known organic reactions, such as, Mannich condensation reactions. As shown in FIG. 1, alkyl sulfonate (i.e., methyl benzenesulfonate) is reacted with formamide in formic acid, paraformaldehyde and toluene to form an intermediate (sulfonyl formamide) product. The reaction can be conducted at various temperatures and typically ranges from about 50° C. to about 110° C., and preferably from about 90° C. to about 110° C. The temperature can be achieved using conventional methods and apparatus in the art. In certain embodiments, microwave heating is employed.

It is contemplated that other suitable acids and solvents known in the art can be used. Non-limiting examples of suitable acids include, but are not limited to, formic acid, acetic acid, proprionic acid, trifluoroacetic acid, chloroacetic acid, toluenesulfonic acid, camphor sulfonic acid, and mixtures thereof. Non-limiting examples of suitable solvents include, but are not limited to, toluene, formaldehyde, paraformaldehyde, dimethyl formamide, dimethylacetamide, hexamethylphosphoramide, dimethylsulphoxide, tetrahydrofuran and mixtures thereof.

The intermediate (formamide) product then undergoes a dehydration reaction to remove the water molecule, such that NH—CHO group in the intermediate product is NC in the final isonitrile product. Various dehydration methods and processes can be used. In accordance with certain embodiments of the invention and as shown in FIG. 1, the intermediate (sulfonyl formamide) product is reacted with a dehydrating agent to form an arylsulfonyl isonitrile product, i.e., ((isocyanomethyl)sulfonyl)benzene (represented by the general structure of Formula II herein, wherein $R^1$, $R^2$, $R^3$, $R^4$ and $R^5$ are each hydrogen). It is contemplated that other suitable solvents and dehydrating agents known in the art can be used. Non-limiting examples of suitable solvents include, but are not limited to, dichloromethane, toluene, chloroform and mixtures thereof. Non-limiting examples of suitable dehydrating agents include, but are not limited to, phosphoryl chloride, triphenylphosphine dichloride, triphenylphosphine dibromide, triphenylphosphinelcarbon tetrabromide, sulfonyl chloride, oxalyl chloride and mixtures thereof. The dehydration step can be conducted at various temperatures and is typically carried out at a temperature within a range from −30° C. to 0° C.

The resulting product may be purified by conventional purification methods and processes known in the art such as, but not limited to, vacuum distillation, flash chromatography, preparative thin layer chromatography and radial chromatography.

As shown in FIG. 2, compounds represented by the general structure of Formula II herein may be used as precursors or building blocks to form other arylsulfonyl isonitriles. For example, compounds of Formula II can be used to prepare arylsulfonyl isonitriles represented by the general structure of Formula III herein. In particular, in FIG. 2, a sulfonylmethyl isonitrile product as shown in FIG. 1, i.e., ((isocyanomethyl)sulfonyl)benzene, undergoes an alkylation reaction to replace the $CH_2$ group bridging the arylsulfonyl and the isonitrile to form a sulfonyl isonitrile product (represented by the general structure of Formula III herein, wherein $R^1$, $R^2$, $R^3$, $R^4$ and $R^5$ are each hydrogen). As shown in FIG. 2, the sulfonylmethyl isonitrile reactant is reacted with the dihalide 1,5-dibromopentane in sodium hydride and dimethyl formamide (DMF). The sodium hydride is typically present in an amount in the range from 2 to 5 equivalents. The alkylation reaction can be conducted at various temperatures and typically the temperature is in the range from −10° C. to room temperature. The time for carrying out the alkylation can also vary and typically is carried out in a time period in the range from 10 hours to 72 hours. It is contemplated that other bases known in the art for use in organic synthesis can be used, such as but not limited to, sodium hydroxide, potassium hexamethyldisilazide, lithium amide, sodium amide and mixtures thereof. Further, it is contemplated that any solvent can be used that is compatible with the base, e.g., sodium hydride, such as but not limited to, dimethylacetamide, hexamethylphosphoramide, dimethylsulphoxide, tetrahydrofuran, toluene and mixtures thereof. It is also contemplated that other dihalide compounds known in the art can be used. Non-limiting examples of suitable dihalides include, but are not limited to, 1,3-dihalopropane, 1,4-dihalobutane, 1,5-dihalopentane, 1,6-dihalohexane and mixtures thereof.

The resulting product may be purified by conventional purification methods and processes known in the art such as, but not limited to, vacuum distillation, flash chromatography, preparative thin layer chromatography and radial chromatography.

Table 1 shows suitable alkyl sulfonates for use in the invention and, arylsulfonyl isonitriles synthesized by suitable formamide synthesis and dehydration methods.

TABLE 1

| Alkyl Sulfonates | |
|---|---|
| 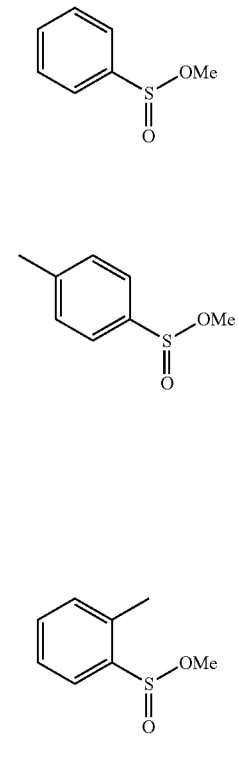 | 4a, 4b, 4c, 4d |
| 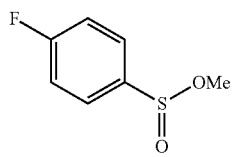 [SMILES: COS(=O)c1ccc(F)cc1] | 4e |
| 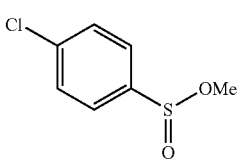 [SMILES: COS(=O)c1ccc(Cl)cc1] | 4f |
| 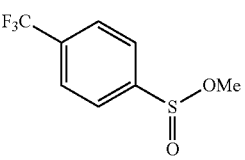 | 4g |
| 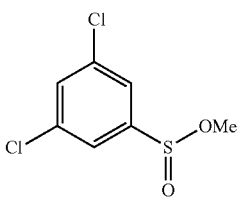 [SMILES: COS(=O)c1cc(Cl)cc(Cl)c1] | 4h |
| 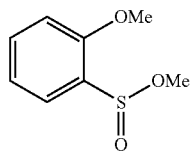 [SMILES: COc1ccccc1S(=O)OC] | 4i |
| 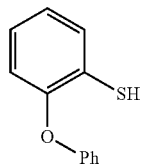 [SMILES: Sc1ccccc1Oc1ccccc1] | t1 |
| 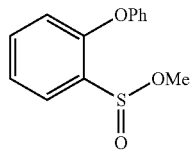 [SMILES: COS(=O)c1ccccc1Oc1ccccc1] | 4j |
| 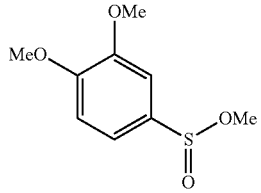 | 4k |
| 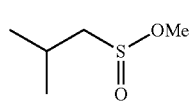 | 4l |

TABLE 1-continued

| Structure | ID |
|---|---|
| cyclohexyl-S(=O)-OMe | 4m |
| Ph-CH2-S(=O)-OMe | 4n |
| 4-Me-C6H4-S(=O)-O-CH2CH2-Ph | 4o |
| 4-Me-C6H4-S(=O)-OEt | s1 |
| 4-Me-C6H4-S(=O)-OiPr | s2 |
| 2,6-dimethoxy-thiophenol | 11p |
| 2-CF3-6-OMe-thiophenol | 11q |
| 2-methoxy-1-naphthalenethiol | 11r |

TABLE 1-continued

Formamide/Dehydration Synthesis
Of Arylsulfonyl Isonitriles

| Structure | ID |
|---|---|
| PhSO2CH2NC | 3a |
| 4-Me-C6H4-SO2CH2NC | 3b |
| 2-Me-C6H4-SO2CH2NC | 3c |
| 2-naphthyl-SO2CH2NC | 3d |
| 4-F-C6H4-SO2CH2NC | 3e |
| 4-Cl-C6H4-SO2CH2NC | 3f |
| 4-CF3-C6H4-SO2CH2NC | 3g |
| 3,5-Cl2-C6H3-SO2CH2NC | 3h |
| 2-OMe-C6H4-SO2CH2NC | 3i |

TABLE 1-continued

| | |
|---|---|
| 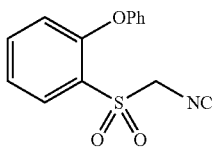 | 3j |
| 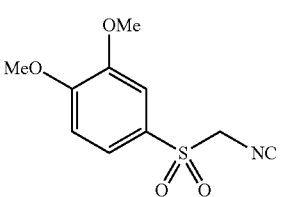 | 3k |
| 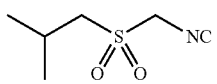 | 3l |
| 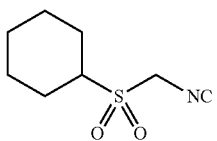 | 3m |
| 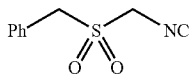 | 3n |
| Oxidizing Formamides | |
| 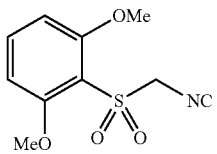 | 3p |
| 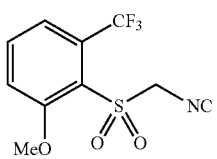 | 3q |
| 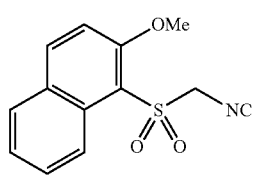 | 3r |
| 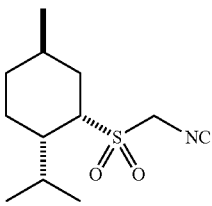 | 3s |
| 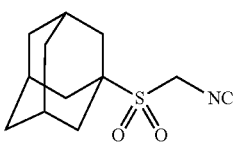 | 3t |

Moreover, other embodiments of the invention will be apparent to those skilled in the art from consideration of the specification and practice of the invention disclosed herein. It is intended that the specification be considered as exemplary only. Furthermore, the following examples are meant to be illustrative of certain embodiments of the invention and are not intended to be limiting as to the scope of the invention.

EXAMPLES

General Experimental Conditions:

Tetrahydrofuran (THE) was freshly distilled from Na/benzophenone ketyl prior to use. Dichloromethane and acetonitrile were dried by passing through an alumina and molecular sieve drying train, commercially available from Innovative Technology Inc. (Model: PS-MD-7). Isopropanol, ethanol and toluene were used as received. Other reagents were purchased at analytical or ACS grade, and used without further purification unless otherwise stated. A Biotage® microwave reactor (Model: Initiator) and 2-20 mL reaction tubes were employed (with the irradiation absorption parameter set to NORMAL). Thin layer chromatography (TLC) was performed with UV active (w/F-254) glass backed silica gel plates (Dynamic Adsorbents Inc.). TLC plates were visualized by exposure to short wavelength UV light (254 inn) and/or staining with a phosphomolybdic acid solution (20% in ethanol) or iodine. Flash chromatography was performed using SiliaFlash® silica gel P60 (30-400 mesh) purchased from Silicycle, Florisil® (100-200 mesh) purchased from Alfa Aesar, or SiliaBond® Diol purchased from Silicycle. Radial chromatography was performed on a Harrison Research Chromatotron™ using rotors covered with $SiO_2$ and leveled to 1, 2, and 4 mm thickness. $^1$H NMR and $^{13}$C NMR high resolution nuclear magnetic resonance spectra were obtained on a Bruker Avance 400 or Bruker Avance 500 spectrometers. $^1$H NMR data are reported as follows: chemical shift, multiplicity (s=singlet, d=doublet, t=triplet, q=quartet, quin=quintet, dd=doublet of doublet, dt=doublet of triplet, ddd=doublet of doublet of doublets, td=triplet of doublets, qd=quartet of doublets, m=multiplet, etc.), integration, and coupling constants (Hz). $^{13}$C NMR data are reported in parts per million (ppm) on the δ scale. High resolution mass spectra (HRMS) were recorded on a 6500 Series Accurate Mass Quadrupole Time of Flight LC/MS using a nano ESI. Infrared spectra were recorded on a Perkin Elmer Frontier FT-IR spectrometer with a universal ATR sampling accessory.

General Sulfinate Synthesis from Thiols

Solid N-bromosuccinimide powder (2 equiv) was added in one portion to a 0° C., methanol:dichloromethane solution (1:1 by volume) of the thiol (1 equiv). The cold bath was removed and, after 1 hour, the mixture was poured into 0° C., saturated NaHCO$_3$ solution. The biphasic mixture was transferred to a separation funnel and shaken until discoloration. The phases were separated and the aqueous layer was extracted with dichloromethane (×3). The combined organic extract was washed with brine, dried (Na$_2$SO$_4$), and concentrated to afford a yellowish crude sulfinate. The crude sulfinate was purified by filtration through a SiO$_2$ plug (10×50 mm) to afford pure methyl sulfinate.

Example 1

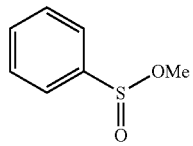

Methyl benzenesulfinate (compound 4a) was prepared from thiophenol (4 g, 36.4 mmol) according to the general sulfinate synthesis affording 5.27 g of compound 4a (93%) as a colorless oil after purification by SiO$_2$ flash chromatography (hexanes:Et$_2$O gradient, 100:0 to 90:10).

Example 2

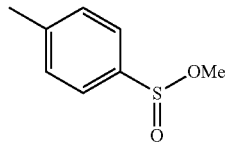

Methyl 4-methylbenzenesulfinate (compound 4b) was prepared from 4-methylbenzenethiol (4 g, 32.2 mmol) according to the general sulfinate procedure to afford 5.3 g of compound 4b (97%) as a colorless oil after purification by filtration on a SiO$_2$ plug (10×50 mm) using hexanes:ethyl ether (90:10) as the eluent.

Example 3

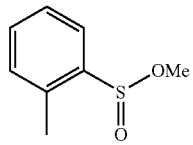

Methyl 2-methylbenzenesulfinate (compound 4c) was prepared from 2-methylbenzenethiol (2 g, 16.1 mmol) according to the general sulfinate procedure to afford 2.7 g of compound 4c (99%) as a slightly amber oil after purification by SiO$_2$ radial chromatography (4 mm rotor using hexanes:EtOAc, 98:2 as the eluent).

Example 4

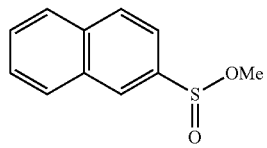 [SMILES: COS(=O)c1ccc2ccccc2c1]

Methyl naphthalene-2-sulfinate (compound 4d) was prepared from 2-naphtalenethiol (2 g. 12.48 mmol) according to the general sulfinate procedure to afford 2.48 g of compound 4d (96%) as slightly yellow crystals after purification by SiO$_2$ column chromatography (hexanes:acetone gradient, 90:10 to 80:20).

Example 5

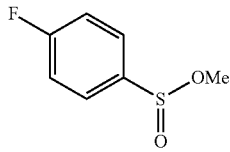

Methyl 4-fluorobenzenesulfinate (compound 4e) was prepared from 4-fluorothiophenol (400 mg, 3.1 mmol) according to the general sulfinate procedure to afford 500 mg of compound 4e (92%) as a colorless oil after purification by SiO$_2$ radial chromatography (2 mm rotor using hexanes: EtOAc:acetone, 80:10:10 as the eluent).

Example 6

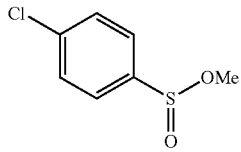 [SMILES: COS(=O)c1ccc(Cl)cc1]

Methyl 4-chlorobenzenesulfinate (compound 4f) was prepared from 4-chlorothiophenol (2 g, 13.8 mmol) according to the general sulfinate procedure to afford 2.3 g of compound 4f (87%) as a colorless oil after purification by SiO$_2$ radial chromatography (4 mm rotor using hexanes:EtOAc, 80:20 as the eluent).

Example 7

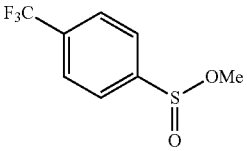 [SMILES: COS(=O)c1ccc(C(F)(F)F)cc1]

Methyl 4-(trifluoromethyl)benzenesulfinate (compound 4g) was prepared from 4-trifluoromethylbenzenethiol (400 mg, 2.25 mmol) according to the general sulfinate procedure to afford 410 mg of compound 4g (82%) as a colorless oil after purification by SiO$_2$ radial chromatography (1 mm rotor using a hexanes:EtOAc as eluent with a gradient ranging from 90:10 to 80:20). $^1$H NMR (400 MHz, benzene-d$_6$) δ 7.32 (d, J=7.8 Hz, 1H), 7.19 (d, J=7.8 Hz, 1H), 2.94 (s, 2H). $^{13}$C NMR (100 MHz, benzene-do) δ 148.53 (s), 133.52 (q, J=32.5 Hz), 126.24, 126.06 (q, J=3.7 Hz), 124.15 (q, J=272.8 Hz), 48.98. IR (ATR) 2949, 1320, 1125, 1058, 959, 698 cm$^{-1}$. HRMS calculated for C$_8$H$_7$F$_3$O$_2$S, 225.0192. found 225.0190 (M+Na)$^+$.

Example 8

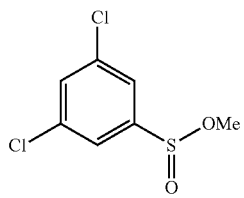 [SMILES: COS(=O)c1cc(Cl)cc(Cl)c1]

Methyl 3,5-dichlorobenzenesulfinate (compound 4h) was prepared according to a published method: Na$_2$CO$_3$ (2.98 g, 28.1 mmol) was added to a cold (0° C.) of 1,2-bis(3,5-dichlorophenyl)disulfane (2 g, 5.62 mmol) in MeOH (112 mL). Bromine (870 μL, 16.8 mmol) was then added dropwise via syringe. After stirring at rt for 3 h, the volatiles were removed in vacuo, the residue was diluted with cold water (100 mL) and EtOAc (100 mL), and the layers were separated. The aqueous layer was extracted with EtOAc (2×100 mL). The combined organic extract was washed with brine, dried (Na$_2$SO$_4$), and concentrated to afford 2.09 g of compound 4h (100%) as a colorless oil which crystallized after purification by filtration through a SiO$_2$ plug using hexanes:Et$_2$O:dichloromethane (90:5:5) as eluent. Mp 55° C. $^1$H NMR (500 MHz, CDCl$_3$) δ 7.58 (d, J=1.9 Hz, 1H), 7.54 (t, J=1.9 Hz, 1H), 3.53 (s, 1H). $^{13}$C NMR (125 MHz, CDCl$_3$) δ 147.37, 136.34, 132.38, 124.12, 50.35. IR (ATR): 3068, 1566, 1132, 958 cm$^{-1}$. HRMS calculated for C$_7$H$_6$Cl$_2$O$_2$S, 224.9538. found 224.9534 (M±H)$^+$.

Example 9

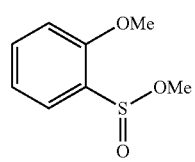 [SMILES: COc1ccccc1S(=O)OC]

Methyl 2-methoxybenzenesulfinate (compound 4i) was prepared from 2-methoxybenzenethiol (8 g, 57.1 mmol) according to the general sulfinate procedure to afford 10.8 g of compound 4i (100%) as a slightly yellow oil after purification by SiO$_2$ column chromatography (hexanes:acetone, 50:50 to 0:100).

Example 10

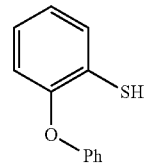

2-Phenoxythiophenol (compound t1) was prepared as follows. Elemental sulfur (565 mg, 17.6 mmol) was added in one portion, under a N$_2$ blanket, to a 0° C., Et$_2$O solution of (2-phenoxyphenyl)lithium. The cooling bath was removed and after 30 min, the mixture was diluted with cold water (100 mL) and then acidified with 2M aqueous HCl until the pH~1. The mixture was left in a freezer (−30° C.) for 20 min and then filtered to afford 2.3 g of a white solid (65%). The crude product was recrystallized from MeOH, to afford 1.7 g (48%) of compound ti as white crystals (mp 63° C.).

Example 11

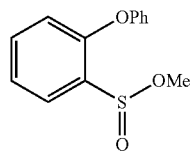

Methyl 2-phenoxybenzensulfinate (compound 4j) was prepared from 2-phenoxythiophenol (1.63 g, 8.06 mmol) according to the general sulfinate procedure to afford 1.81 g of compound 4j (91%) as a colorless oil after purification by filtration through a SiO$_2$ plug (10×50 mm, using a hexanes:dichloromethane:Et$_2$O gradient 90:5:5 to 80:10:10). $^1$H NMR (500 MHz, Chloroform-d) δ 7.94 (dd, J=7.8, 1.7 Hz, 1H), 7.50-7.42 (m, 1H), 7.37 (dd, J=8.6, 7.3 Hz, 2H), 7.27 (td, J=7.6, 1.0 Hz, 1H), 7.20-7.15 (m, 1H), 7.04 (d, J=7.9 Hz, 2H), 6.89 (d, J=8.1 Hz, 1H), 3.59 (s, 3H). $^{13}$C NMR (125 MHz. Chloroform-d) δ 156.16, 155.52, 134.17, 133.84, 130.07, 126.25, 124.47, 123.35, 119.44, 118.27, 51.36. IR (ATR) 2940, 1581, 1465, 1227, 1120, 965, 691. HRMS calculated for C$_{13}$H$_{12}$O$_3$S, 271.0399. found 271.0401 (M+Na)+.

Example 12

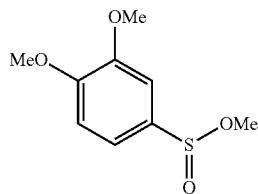 [SMILES: COc1ccc(S(=O)OC)cc1OC]

Methyl 3,4-dimethoxybenzenesulfinate (compound 4k) was prepared as follows. Methanol (8.8 mL) and dry pyridine (3.5 mL, 43.4 mmol) were added sequentially to a flask immersed in an ice bath containing freshly prepared 3,4-dimethoxybenzenesulfinyl chloride (1.6 g, 7.24 mmol). After 2 h, the reaction was diluted with cold aqueous NaHCO$_3$ and extracted with dichloromethane (4×10 mL). After removal of the volatiles, 1.21 g (77%) of relatively pure compound 4k were recovered as a slightly yellow oil: $^1$H NMR (400 MHz, Chloroform-d) δ 7.28 (dd, J=8.3, 2.0 Hz, 1H), 7.23 (d, J=2.0 Hz, 1H), 7.01 (d, J=8.3 Hz, 1H), 3.96 (s, 3H), 3.95 (s, 3H), 3.48 (s, 3H). $^{13}$C NMR (100 MHz, Chloroform-d) δ 152.18, 149.48, 135.60, 118.91, 110.87, 107.27, 56.13, 56.12, 49.28. IR (ATR) 2940, 2839, 1504, 1256, 1231, 1117, 1019, 957, 672 cm$^{-1}$. HRMS calculated for C$_9$H$_{12}$O$_4$S, 239.0348. found 239.0350 (M+Na)$^+$.

Example 13

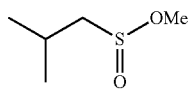

Methyl 2-methylpropane-1-sulfinate (compound 4l) was prepared from isobutyl mercaptan (3 g, 33.27 mmol) according to the general sulfinate procedure to afford 3.97 g of compound 4l (88%) as a colorless oil after purification by SiO$_2$ flash chromatography (hexanes:dichloromethane, 90:10 as eluent): $^1$H NMR (500 MHz, Chloroform-d) δ 3.78 (s, 3H), 2.69 (dd, J=13.2, 7.6 Hz, 1H), 2.61 (dd, J=13.2, 6.6 Hz, 1H), 2.14 (nontuplet, J=6 Hz, 1H), 1.07 (d, J=3.0 Hz, 3H), 1.06 (d, J=2.9 Hz, 3H); $^{13}$C NMR (125 MHz, Chloroform-d) δ 65.89, 54.41, 23.61, 22.68, 22.33. IR (ATR): 2962, 1125, 992, 684 cm'; HRMS calculated for C$_5$H$_{12}$O$_2$S, 159.0450. found 159.0444 (M+Na)$^+$.

Example 14

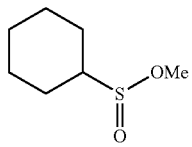

Methyl cyclohexanesulfinate (compound 4m) was prepared from cyclohexanethiol (2 g, 17.2 mmol) according to the general sulfinate procedure to afford 2.92 g of compound 4m (quant.) as a colorless oil after purification by SiO$_2$ flash chromatography (hexanes:Et$_2$O:dichloromethane, 90:5:5 as eluent). $^1$H NMR (500 MHz, Chloroform-d) δ 3.78 (s, 3H), 2.56 (tt, J=11.7, 3.7 Hz, 1H), 2.06-1.94 (m, 2H), 1.93-1.81 (m, 1H), 1.74-1.65 (m, 1H), 1.46-1.18 (m, 6H); $^{13}$C NMR (125 MHz, Chloroform-d) δ 63.44, 54.95, 25.56, 25.12, 25.03, 24.42, 24.03. IR (ATR): 2930, 1450, 1129, 689 cm'; HRMS calculated for C$_7$H$_{14}$O$_2$S, 163.0787. found 163.0790 (M+H)$^+$.

Example 15

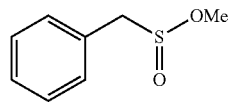 [SMILES: COS(=O)Cc1ccccc1]

Methyl phenylmethanesulfinate (compound 4n) was prepared from benzylmercaptan (3 g, 24.15 mmol) according to the general sulfinate procedure to afford 3.41 g of compound 4n (83%) as a colorless oil after purification by SiO$_2$ flash chromatography (hexanes:dichloromethane 95:5 then hexanes:dichloromethane:Et$_2$O 90:5:5).

Example 16

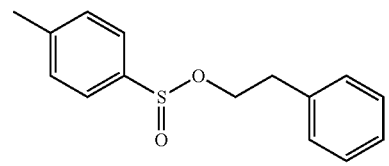 [SMILES: Cc1ccc(S(=O)OCCc2ccccc2)cc1]

Phenethyl 4-methylbenzenesulfinate (compound 4o) Dicyclohexylcarbodiimide (0.436 g, 2.11 mmol), 2-phenylethanol (250 µL, 21.11 mmol) and were sequentially added to a rt, dichloromethane solution (2.1 mL) of p-toluenesulfinic acid (0.33 g, 2.11 mmol). After 4 h, the mixture was diluted with aqueous NaHCO$_3$ (4 mL) and Et$_2$O (4 mL). The mixture was filtered and the solid was washed with Et$_2$O (2 mL). The organic layer was collected and the aqueous was extracted with Et$_2$O (2×4 mL). The organic extracts were dried (Na$_2$SO$_4$) and concentrated and the crude sulfinate purified by SiO$_2$ flash chromatography (hexanes:EtOAc, gradient 90:10 to 85:15) to afford 501 mg (91%) of compound 4o as a clear, colorless oil.

Example 17

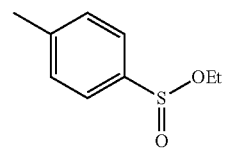

Ethyl 4-methylbenzenesulfinate (compound s1) was prepared from 4-methylbenzenethiol (2.33 g, 18.8 mmol) according to the general sulfinate procedure with the modification of using ethanol instead of methanol, to afford 3.38 g of compound s1 (98?/o) as a colorless oil after purification by SiO$_2$ flash chromatography (hexanes:Et$_2$O:CH$_2$Cl$_2$ gradient (95:5:5 to 70:20:10).

Example 18

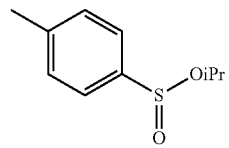

Isopropyl 4-methylbenzenesulfinate (compound s2) was prepared from 4-methylbenzenethiol (2.18 g, 17.6 mmol) according to the general sulfinate procedure with the modification of using i-PrOH instead of methanol, adding K$_2$CO$_3$ (2.43 g, 17.6 mmol) immediately prior to the NBS, and extending the reaction time to 2.5 h. The modified procedure afforded 2.32 g (67%) of compound s3 as a colorless oil after SiO$_2$ flash chromatography (hexanes:Et$_2$O:CH$_2$Cl$_2$ 95:5:5, then Et$_2$O: CH$_2$Cl$_2$ 50:50).

Example 19

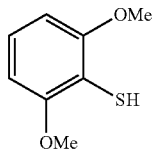 [SMILES: COc1cccc(OC)c1S]

2,6-dimethoxybenzenethiol (compound 11p) was prepared as follows. Elemental sulfur (2.09 g, 65.1 mmol) was added in one portion, under a N$_2$ 12 blanket, to a 0° C. suspension of (2,6-dimethoxyphenyl)lithium in hexanes. After stirring the mixture overnight at rt, the mixture was diluted with water (100 mL) and then acidified with 1M aqueous HCl until a pH ~1. The mixture was cooled to 0° C. and after 30 min the solid was filtered and collected. The material was recrystallized from MeOH to afford 9.48 g (77%) of compound 11p.

Example 20

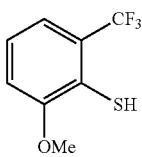

2-methoxy-6-(trifluoromethyl)benzenethiol (compound 11 q) Elemental sulfur (2.73 g, 85.16 mmol) was added in small portions, under a N$_2$ blanket, to a 0° C., THF solution of (2-methoxy-6-(trifluoromethyl)phenyl)lithium. After 30 min, the reaction was diluted with cold water (25 mL) and then acidified with 2M aqueous HCl until a pH ~1. The phases were separated, the aqueous was extracted with dichloromethane (3×30 mL), and the extracts were then combined. The crude thiol was concentrated and was then purified by filtration on a SiO$_2$ plug using hexanes as the eluant to afford 9.62 g (81%) of 11q as a slightly yellow oil.

Example 21

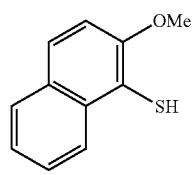

2-Methoxynaphthalene-1-thiol (compound 11r) was prepared as follows. (Preparation of (2-methoxynaphthalen-1-yl)magnesium bromide) A THF solution (8 mL) of 1-bromo-2-methoxynaphtalene (4 g, 16.87 mmol) was added, dropwise, to a THF slurry (17 mL) of magnesium turnings (533 g, 21.93 mmol) that had been previously activated through the addition of 1,2-dibromoethane (150 µL, 1.69 mmol). The flask was gently heated with a heat gun, while avoiding boiling. After 30 min, the flask was irradiated at rt in an ultrasonic cleaning bath for 2.5 h to afford a THF solution of the Grignard reagent. Elemental sulfur (0.757 g, 23.62 mmol) was added in one portion, under a N$_2$ blanket, to the 0° C. solution of (2-methoxynaphtalen-1-yl)magnesium bromide (vide supra). After 30 min, lithium aluminum hydride powder (0.32 g, 8.44 mmol) was added in very small portions. After 30 min, the reaction was diluted with cold, aqueous, saturated NH$_4$Cl (20 mL) and then aqueous citric acid 2M (5 mL). The mixture was extracted with dichloromethane (3×30 mL) and, after the removal of volatiles, the resulting slightly yellow solid was partially dissolved with pentane. The pentane solution was cooled by immersion into a −78° C. cooling bath and after 5 min the temperature was raised to 0° C. After 15 min the solution was filtered to afford 3.01 g (94%) of compound 11r as a white crystalline solid: Mp 66-67° C. (lit. 65-68° C.). $^1$H NMR (400 MHz, Chloroform-d) δ 7.98 (dd, J=8.5, 0.9 Hz, 1H), 7.74 (d, J=8.2 Hz, 1H), 7.61 (d, J=9.0 Hz, 1H), 7.49 (ddd, J=8.4, 6.8, 1.3 Hz, 1H), 7.34 (ddd, J=8.0, 6.8, 1.1 Hz, 1H), 7.19 (d, J=8.9 Hz, 1H), 4.39 (s, 1H), 3.95 (s, 3H); $^{13}$C NMR (100 MHz, Chloroform-d) δ 151.51, 132.01, 129.28, 128.43, 126.64, 126.28, 124.04, 123.98, 114.72, 112.71, 56.82; IR (ATR) 3052, 2937, 2838, 2579, 1506, 1265, 1247, 1075, 797, 767, 741 cm$^{-1}$; HRMS calculated for C$_{22}$H$_{18}$O$_2$S$_2$ (disulfide) 401.0640. found 401.0648 (M+Na)$^+$.

General Formamide Synthesis A—Conventional Heating

Paraformaldehyde (4 eq), formamide (7.5 eq) and formic acid (5 eq) were sequentially added to neat methyl sulfinate (1 eq) and then the flask was immersed in a pre-heated oil bath (90-100° C.). After 2-3 h the mixture was diluted with cold water and extracted with EtOAc (×4). The combined organic extract was washed once with brine, dried (Na$_2$SO$_4$), and concentrated to afford the crude formamide. The material was dried for 2 h under high vacuum before performing the dehydration.

General Formamide Synthesis B—Microwave Heating

A Biotage® Microwave vial was charged sequentially with paraformaldehyde (5 eq), formamide (6 eq), formic acid (5 eq) and toluene (5 eq). The vial was capped, purged three times with N$_2$ by a gas inlet and a needle vent, and then the flask was heated at 100° C. After 3 h, the mixture was allowed to cool, diluted with cold water, and extracted with EtOAc (×4). The combined organic extract was washed once with brine, dried (Na$_2$SO$_4$), and concentrated to afford the crude formamide. The material was dried for 2 h under high vacuum before performing the dehydration.

General Dehydration Method

Dry diisopropylamine or dry triethylamine (9.3 equiv) were sequentially added dropwise to a −20° C., THF: acetonitrile solution (0.3 M, 2:1 mixture) of the crude formamide (1 eq). After 1 h, while maintaining the temperature below −10° C., the reaction was diluted with cold, aqueous NaHCO$_3$ and then the phases were separated. The mixture was extracted with dichloromethane (×4), the combined organic extract was washed with brine, dried (Na$_2$SO$_4$), and concentrated to afford the crude isonitrile. The crude isonitrile was filtered through a SiO$_2$ plug (10×50 mm) and then purified by SiO$_2$ flash chromatography or SiO$_2$ radial chromatography to afford the pure isonitrile.

Example 22

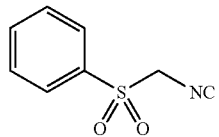

Figure 3:
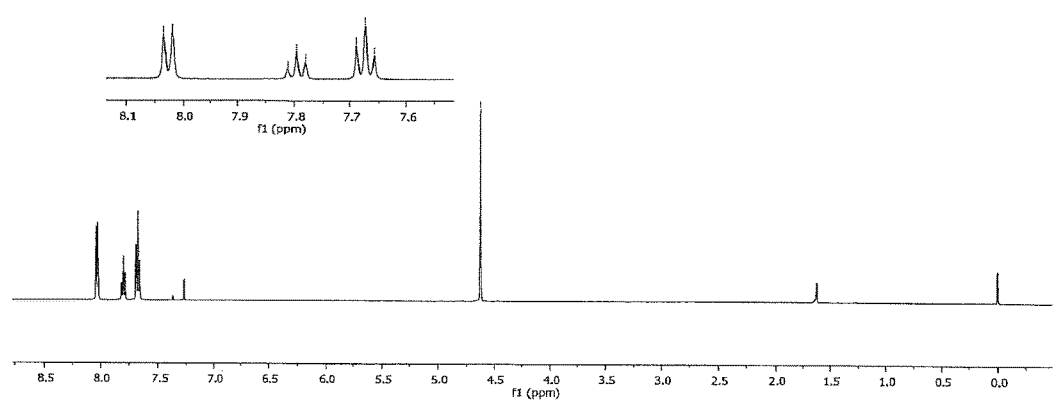
FIG. 3 illustrates NMR data relating to the synthesis ((isocyanomethyl)sulfonyl) benzene, in accordance with certain embodiments of the invention.

((Isocyanomethyl)sulfonyl)benzene (compound 3a) was prepared as follows. The sulfonyl formamide 2a was prepared from methyl benzenesulfinate 4a (500 mg, 3.2 mmol) following the general method B. Subsequent dehydration following the general method with i-Pr$_2$NH afforded 419 mg (72%) of compound 3a as a white solid after purification by SiO$_2$ radial chromatography (2 mm rotor, hexanes:EtOAc 90:10 to hexanes:EtOAc:dichloromethane 60:20:20): Mp 89-90° C. (lit. 88° C.); $^1$H NMR (500 MHz, Chloroform-d) δ 8.03 (d, J=7.2 Hz, 2H), 7.80 (t, J=7.6 Hz, 1H), 7.67 (t, J=7.8 Hz, 2H), 4.62 (s, 2H); $^{13}$C NMR (125 MHz, Chloroform-d) δ 166.38, 135.58, 135.14, 129.88, 129.54, 61.13; IR (ATR) 3058, 2985, 2933, 2151 (lit. 2150 cm$^{-1}$), 1583, 1158; FIRMS calculated for C$_8$H$_7$NO$_2$S, 204.0090. found 204.0091 (M+Na)$^+$. See FIG. 3.

Example 23

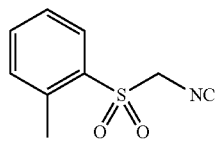

1-((isocyanomethyl)sulfonyl)-4-methylbenzene (TosMIC) (compound 3b) was prepared as follows. The sulfonyl formamide 2b was prepared from methyl 4-methylbenzenesulfinate 4b (0.5 g, 2.94 mmol) following the general method B. Subsequent dehydration of 2b following the general method with i-Pr$_2$NH afforded 0.406 g (71%) of compound 3b as a white solid after purification by SiO$_2$ radial chromatography (2 mm rotor, hexanes:EtOAc, 70:30, as eluent): Mp 112-113° C. (lit. 116-117° C.).

Example 24

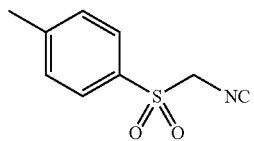

1-((isocyanomethyl)sulfonyl-2-methylbenzene (compound 3c) was prepared as follows. The sulfonyl formamide 2c was prepared from methyl 2-methylbenzenesulfinate 4c (0.5 g, 2.94 mmol) according to the general method B. Subsequent dehydration of 2c with i-Pr$_2$NH following the general dehydration method afforded 325 mg (57%) of compound 3c as a yellowish oil after purification by SiO$_2$ radial chromatography (2 mm thickness rotor, hexanes: EtOAc, gradient 90:10 to 60:40): $^1$H NMR (400 MHz, Chloroform-d) δ 8.08 (dd, J=8.0, 1.4 Hz, 1H), 7.63 (td, J=7.6, 1.4 Hz, 1H), 7.46 (tdd, =7.4, 1.3, 0.6 Hz, 1H), 7.42 (ddt, J=7.6, 1.3, 0.6 Hz, 1H), 4.66 (s, 2H), 2.74 (s, 3H); $^{13}$C NMR (100 MHz, Chloroform-d) δ 166.23, 139.30, 135.46, 133.42, 133.18, 132.18, 127.20, 60.55, 20.83; IR (ATR) 2936, 2146, 1330, 1152, 748; HRMS calculated for C$_9$H$_9$NO$_2$S, 218.0246. found 218.0244 (M+Na)$^+$.

Example 25

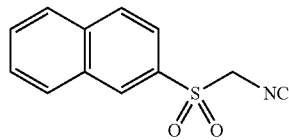

Figure 4:
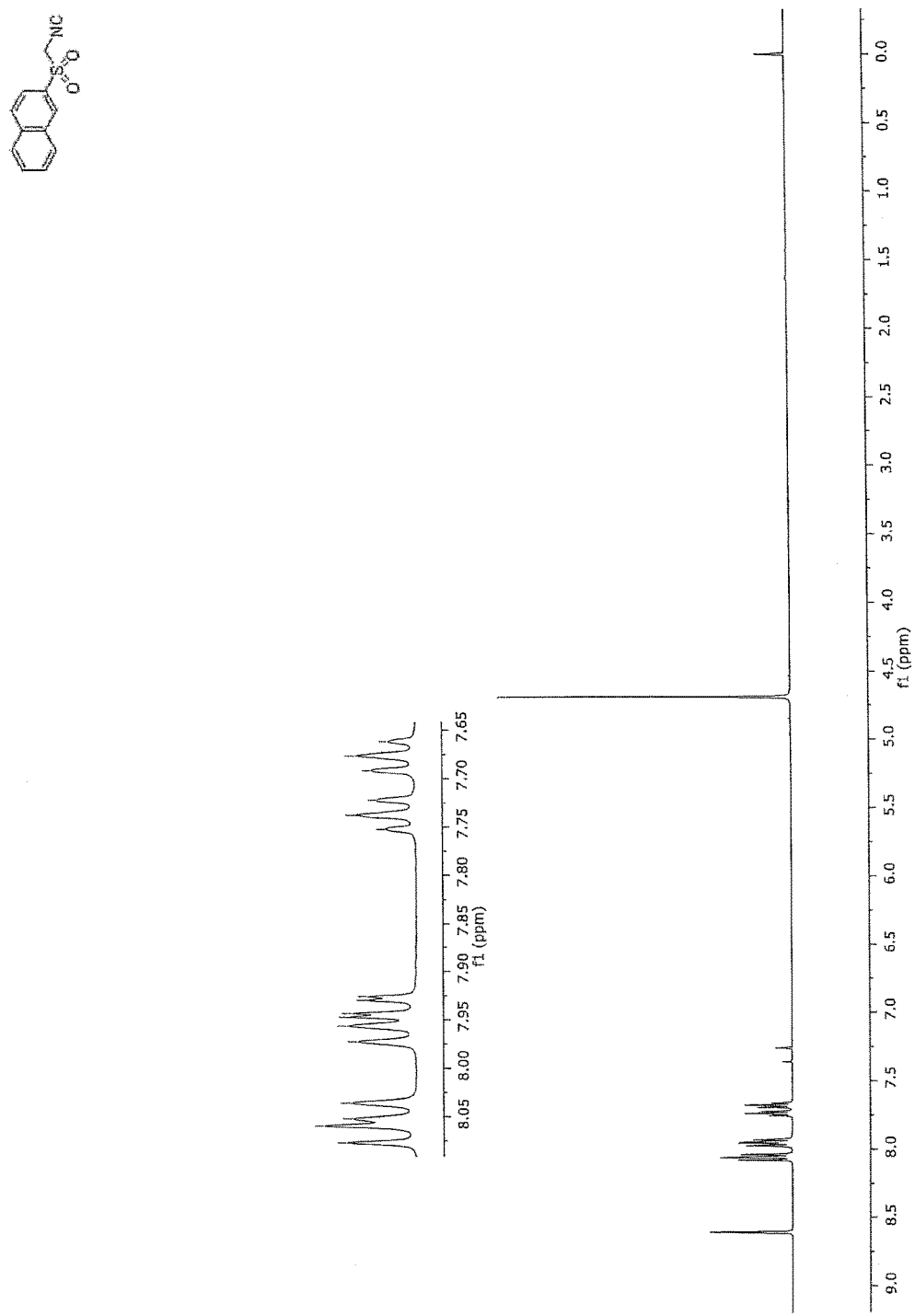
FIGS. 4 and 5 illustrate NMR data relating to the synthesis of 2-((isocyanomethyl)sulfonyl)naphthalene, in accordance with certain embodiments of the invention.
Figure 5:
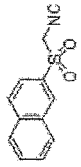
Figure 5:
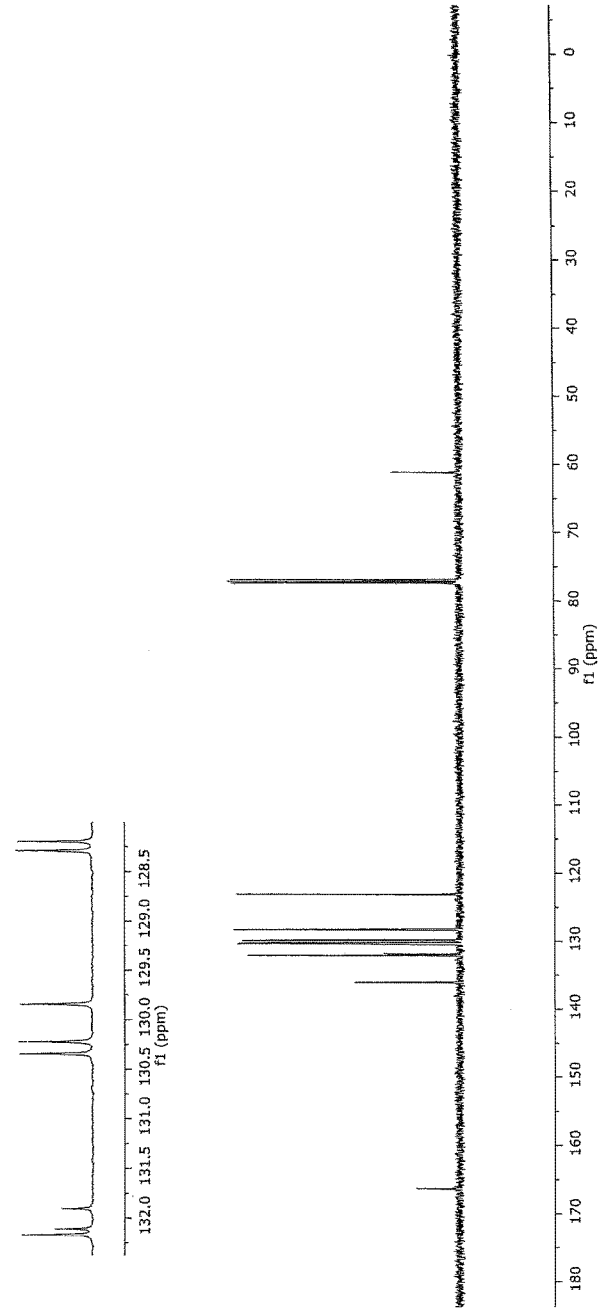

2-((isocyanomethyl)sulfonyl)naphthalene (compound 3d) was prepared as follows. The sulfonyl formamide 2d was prepared from methyl 2-naphthylsulfinate 4d (0.5 g, 2.42 mmol) following general method A and with the modification of heating for 2 h at 90° C. The resulting formamide 2d was dehydrated following the general method with i-Pr$_2$NH to afford 390 mg (70%) of compound 3d as a white solid after purification by SiO$_2$ radial chromatography (hexanes: EtOAc 90:10 to hexanes:EtOAc/dichloromethane 60:20: 20): Mp 104-105° C.; $^1$H NMR (500 MHz, Chloroform-d) δ 8.61 (s, 1H), 8.07 (d, J=8.8 Hz, 1H), 8.04 (d, J=8.4 Hz, 1H), 7.96 (d, J=8.3 Hz, 1H), 7.94 (dd, J=8.7, 1.9 Hz, 1H), 7.74 (t, J=6.9 Hz, 1H), 7.68 (t, J=7.0 Hz, 1H), 4.69 (s, 3H); $^{13}$C NMR (125 MHz, Chloroform-d) δ 166.32, 136.09, 132.17, 132.11, 131.90, 130.35, 130.22, 129.84, 128.29, 128.20, 123.11, 61.16; IR (ATR) 3059, 2989, 2934, 2146, 1330, 1129, 1072, 754; HRMS calculated for C$_{12}$H$_9$NO$_2$S, 232.0427. found 232.0431 (M+H)$^+$. See FIGS. 4 and 5.

Example 26

Figure 6:
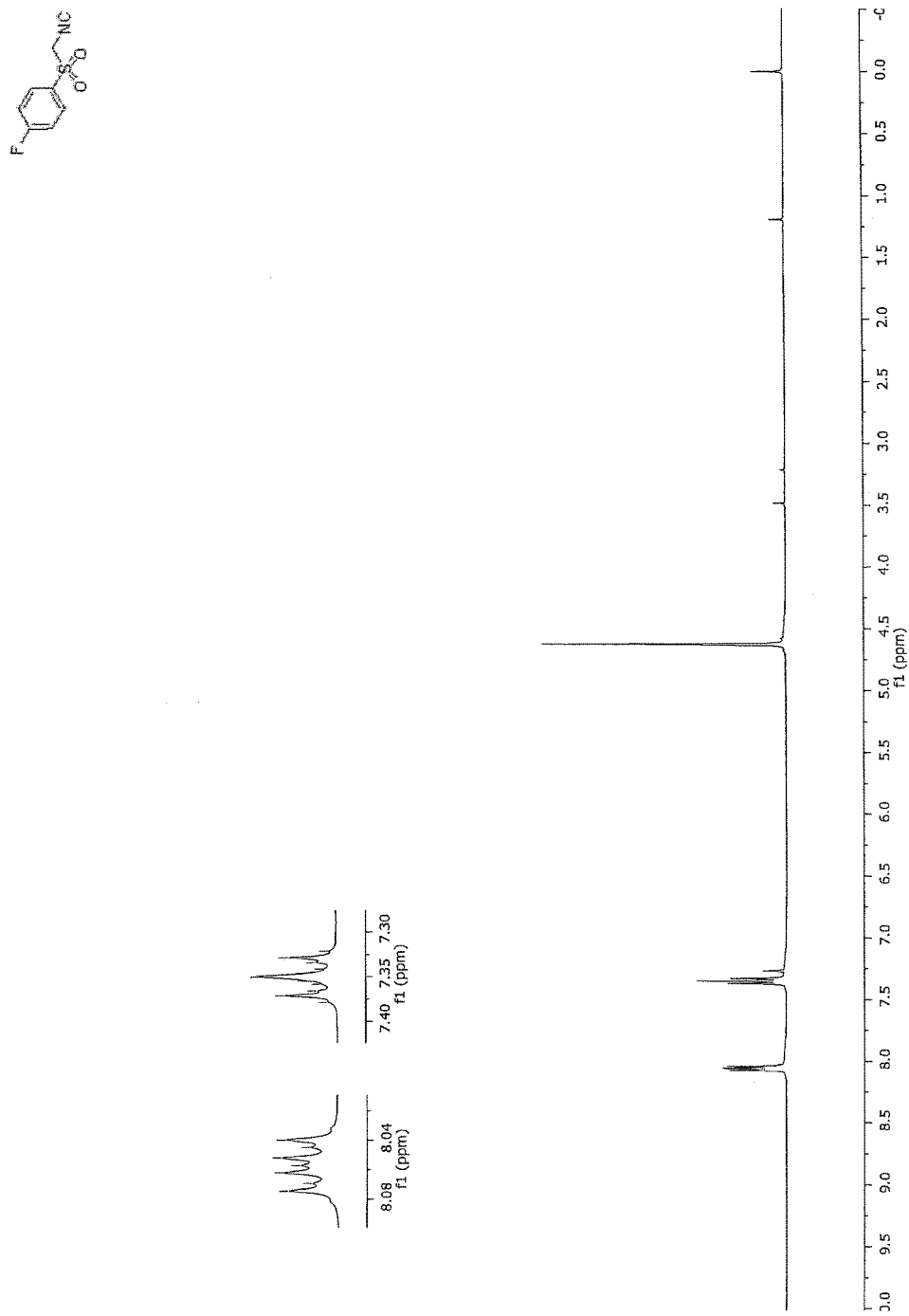
FIGS. 6 and 7 illustrate NMR data relating to the synthesis of 1-fluoro-4-((isocyanomethyl)sulfonyl)benzene, in accordance with certain embodiments of the invention.
Figure 7:
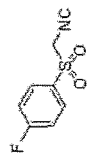
Figure 7:
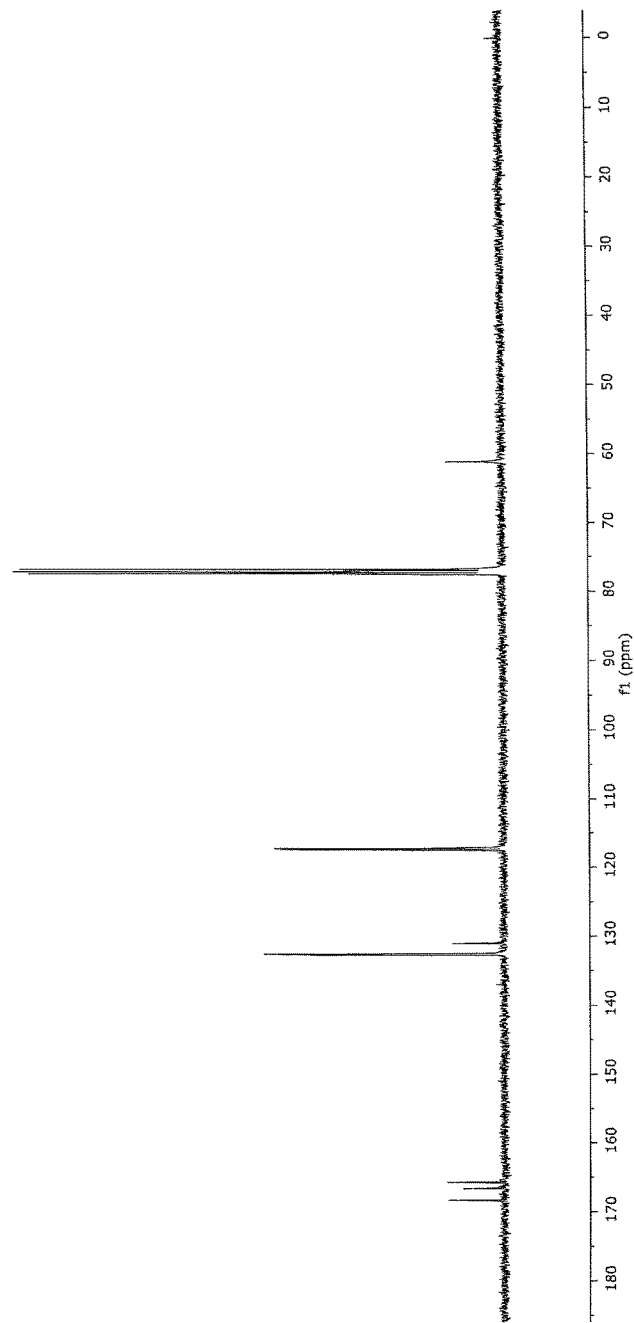

1-fluoro-4-((isocyanomethyl)sulfonyl)benzene (compound 3e) was prepared as follows. The sulfonyl formamide 2e was prepared from methyl 4-fluorobenzenesulfinate 4e (0.2 g, 1.15 mmol) following general method B with the modification of heating for 3 h at 100° C. Crude 2e was dehydrated following the general method with i-Pr$_2$NH to afford 0.155 g (81%) of compound 3e as a slight amber solid after purification on SiO$_2$ (radial chromatography, 1 mm rotor, hexanes:EtOAc gradient 90:10 to 80:20): Mp 63° C.; $^1$H NMR (400 MHz, Chloroform-d) δ 8.09-8.01 (m, 2H), 7.40-7.30 (m, 2H), 4.63 (s, 2H); $^{13}$C NMR (100 MHz, Chloroform-d) δ 167.03 (d, J=259.6 Hz), 166.62, 132.66 (d, J=10.1 Hz), 131.06 (d, J=3.2 Hz), 117.40 (d, J=22.9 Hz), 61.21; IR (ATR) 2992, 2147, 1338, 1147 cm$^{-1}$; HRMS calculated for C$_8$H$_6$FNO$_2$S, 200.0176. found 200.0174 (M+Na)$^+$. See FIGS. 6 and 7.

Example 27

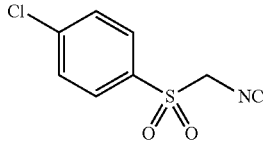

Figure 8:
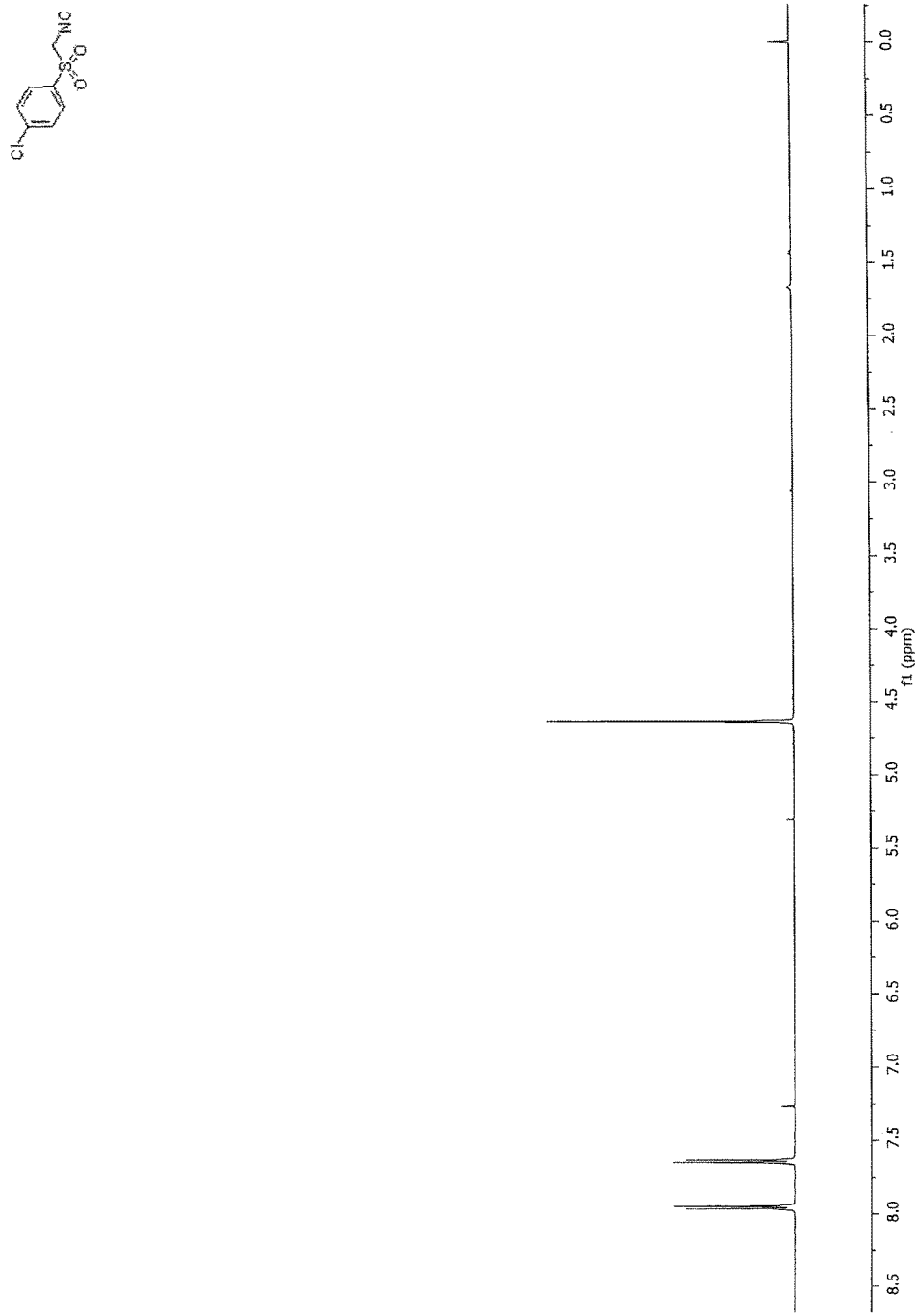
FIGS. 8 and 9 illustrate NMR data relating to the synthesis of 1-chloro-4-((isocyanomethyl)sulfortyl)benzene, in accordance with certain embodiments of the invention.
Figure 9:
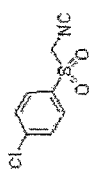
Figure 9:
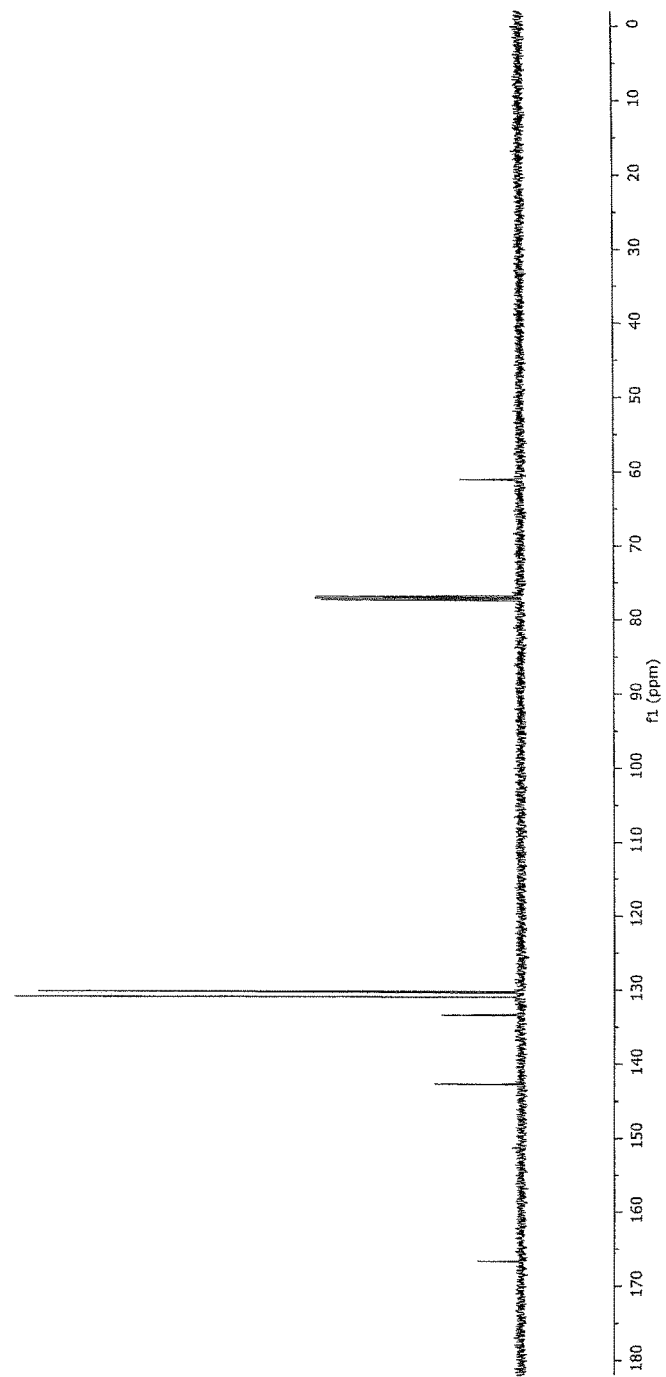

1-Chloro-4-((isocyanomethyl)sulfonyl)benzene (compound 3f) was prepared as follows. The sulfonyl formamide 2f was prepared from methyl 4-chlorobenzenesulfinate 4f (500 mg, 2.62 mmol) following general method B with the modification of heating for 3 h at 105° C. The crude formamide 2f was dehydrated following the general method with i-Pr$_2$NH to afford 399 mg (71%) of compound 3f as a white solid after purification on SiO$_2$ (radial chromatography, 2 mm rotor, hexanes:Et$_2$O:dichloromethane gradient 90:5:5 to 60:20:20); mp. 109-110 (dec); $^1$H NMR (500 MHz, Chloroform-d) δ 7.96 (d, J=8.7 Hz, 1H), 7.64 (d, J=8.7 Hz, 1H), 4.64 (s, 1H); $^{13}$C NMR (126 MHz, Chloroform-d) δ 166.67, 142.69, 133.43, 130.98, 130.27, 61.12. IR (ATR) 3006, 2152, 1323, 1151, 1082 cm$^{-1}$; HRMS calculated for C$_8$H$_6$C$_1$NO$_2$S, 237.9702. found 237.9702 (M+Na)$^+$. See FIGS. 8 and 9.

Example 28

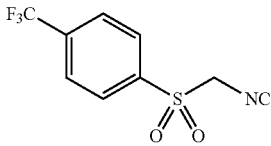

Figure 10:
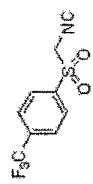
FIGS. 10 and 11 illustrate NMR data relating to the synthesis of 1-((isocyanomethyl)sulfonyl)-4-(trifluoromethyl)benzenesulfinate, in accordance with certain embodiments of the invention.
Figure 10:
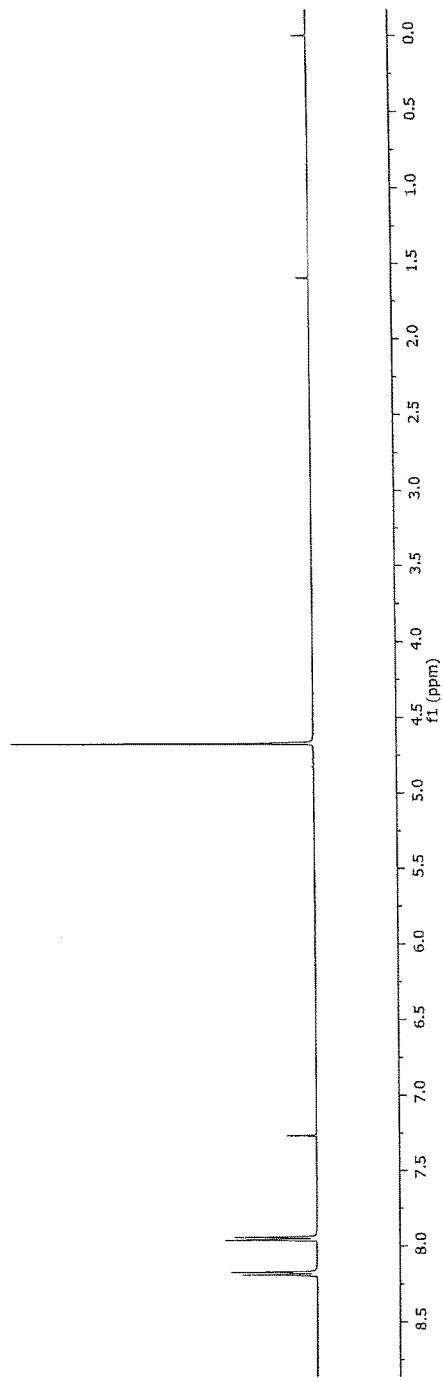
Figure 11:
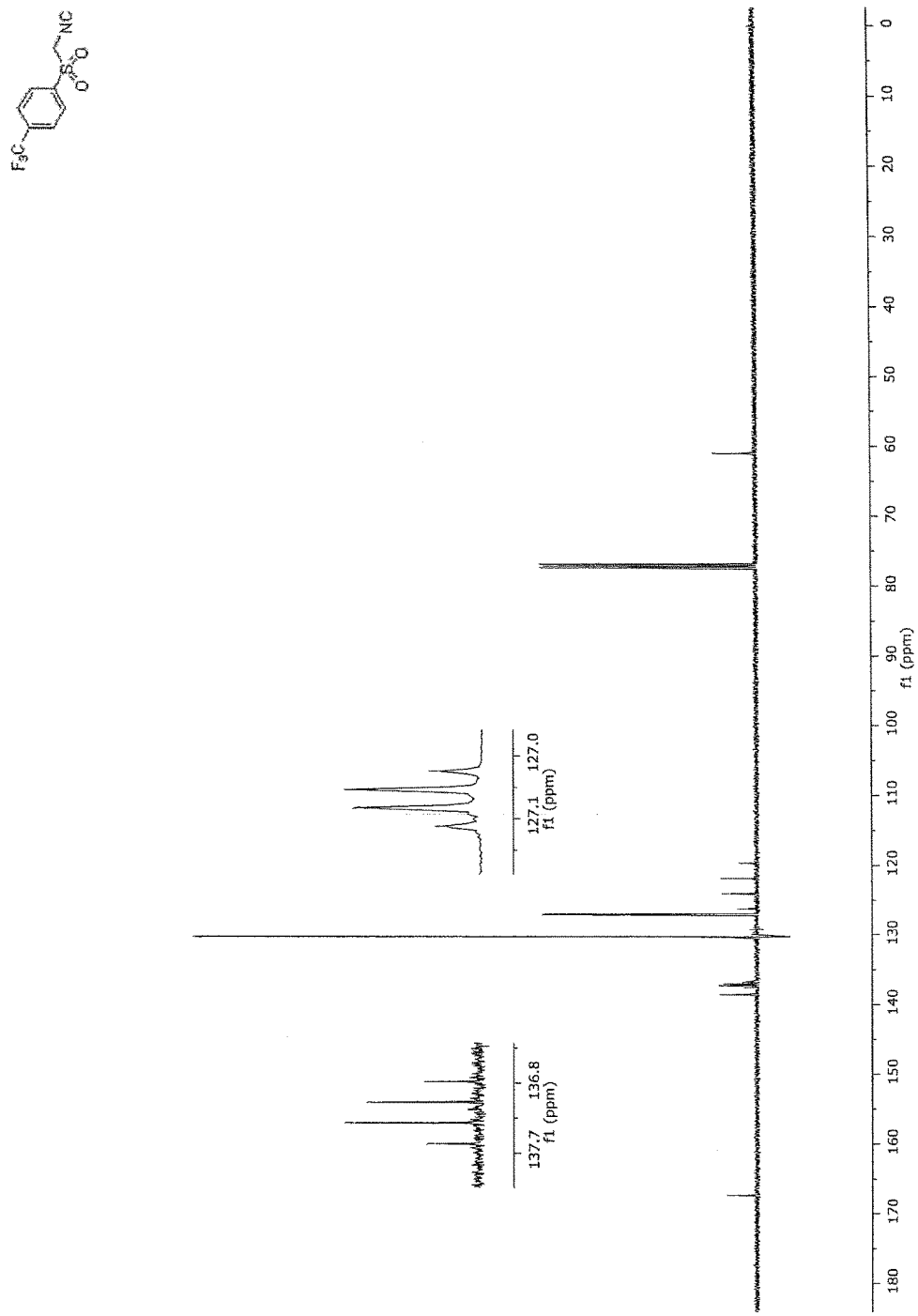

1-((isocyanomethypsulfonyl)-4-(trifluoromethyl)benzenesulfinate (compound 3g) was prepared as follows. The sulfonyl formamide 2g was prepared from methyl 4-(trifluoromethyl)benzene sulfinate 4g (500 mg, 2.23 mmol) following general method A. Crude 2g was dehydrated following the general method with Et$_3$N to afford 316 mg (57%) of compound 3g as a white solid after purification on SiO$_2$ (flash chromatography using hexanes:Et$_2$O gradient 90:10 to 80:20); mp. 104-105° C. (dec); $^1$H NMR (500 MHz, Chloroform-d) δ 8.18 (d, J=8.2 Hz, 2H), 7.95 (d, J=8.2 Hz, 2H), 4.67 (s, 3H); $^{13}$C NMR (125 MHz, Chloroform-d) δ 167.31, 138.59, 137.18 (q, J=33.5 Hz), 130.30, 127.07 (q, J=3.7 Hz), 122.95 (q, J=274.5 Hz), 61.03; IR (ATR) 2987, 2933, 2149, 1323, 1165, 1134, 1147, 1108, 843 cm$^{-1}$; HRMS calculated for C$_9$H$_6$F$_3$NO$_2$S, 271.9964. found 271.9964 (M+Na)$^+$. See FIGS. 10 and 11.

Example 29

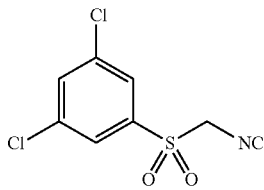

Figure 12:
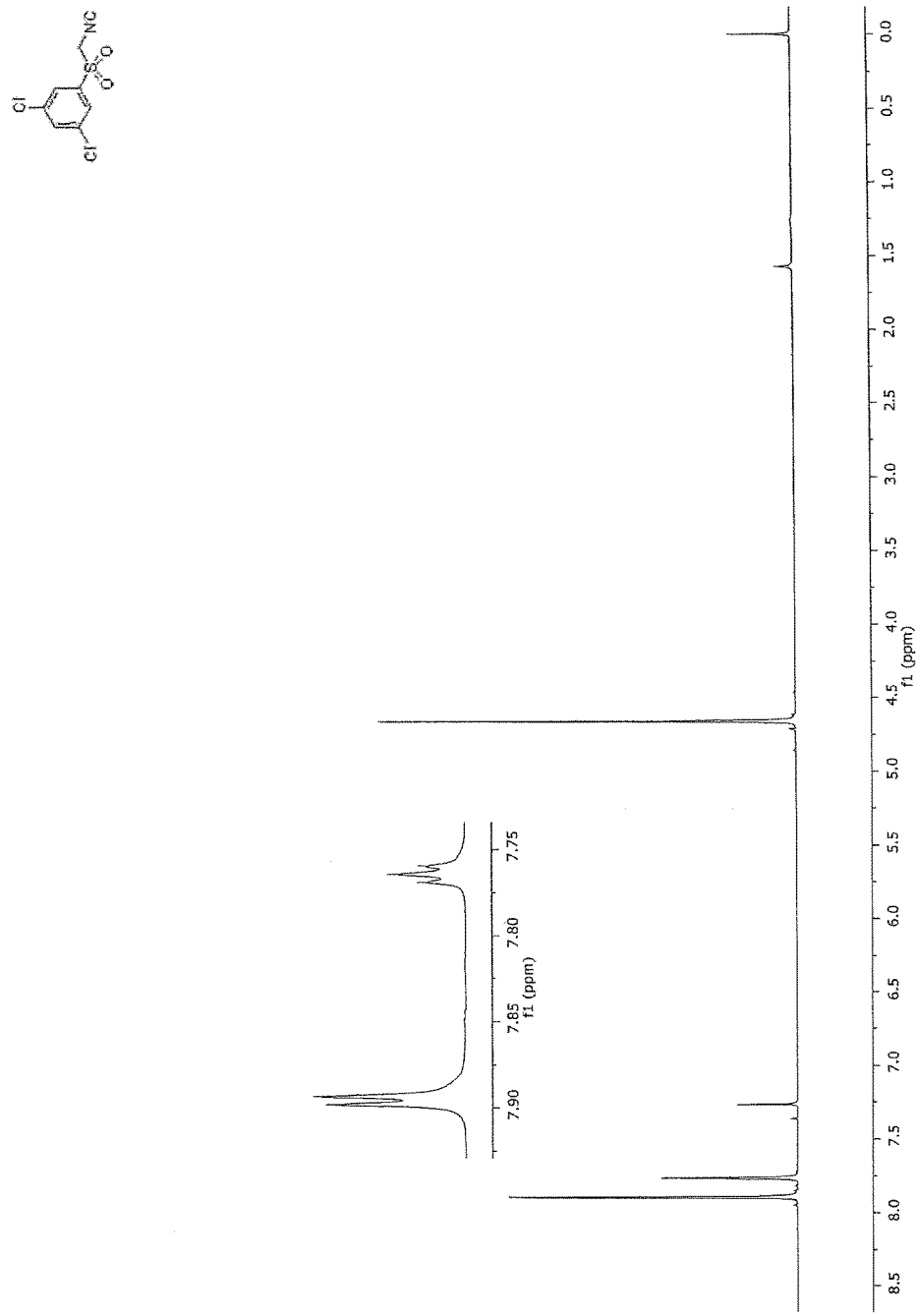
FIGS. 12 and 13 illustrate NMR data relating to the synthesis of 1,3-dichloro-5-((isocyanomethyl)sulfonyl)benzene, in accordance with certain embodiments of the invention.
Figure 13:
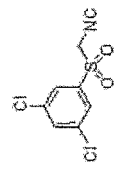
Figure 13:
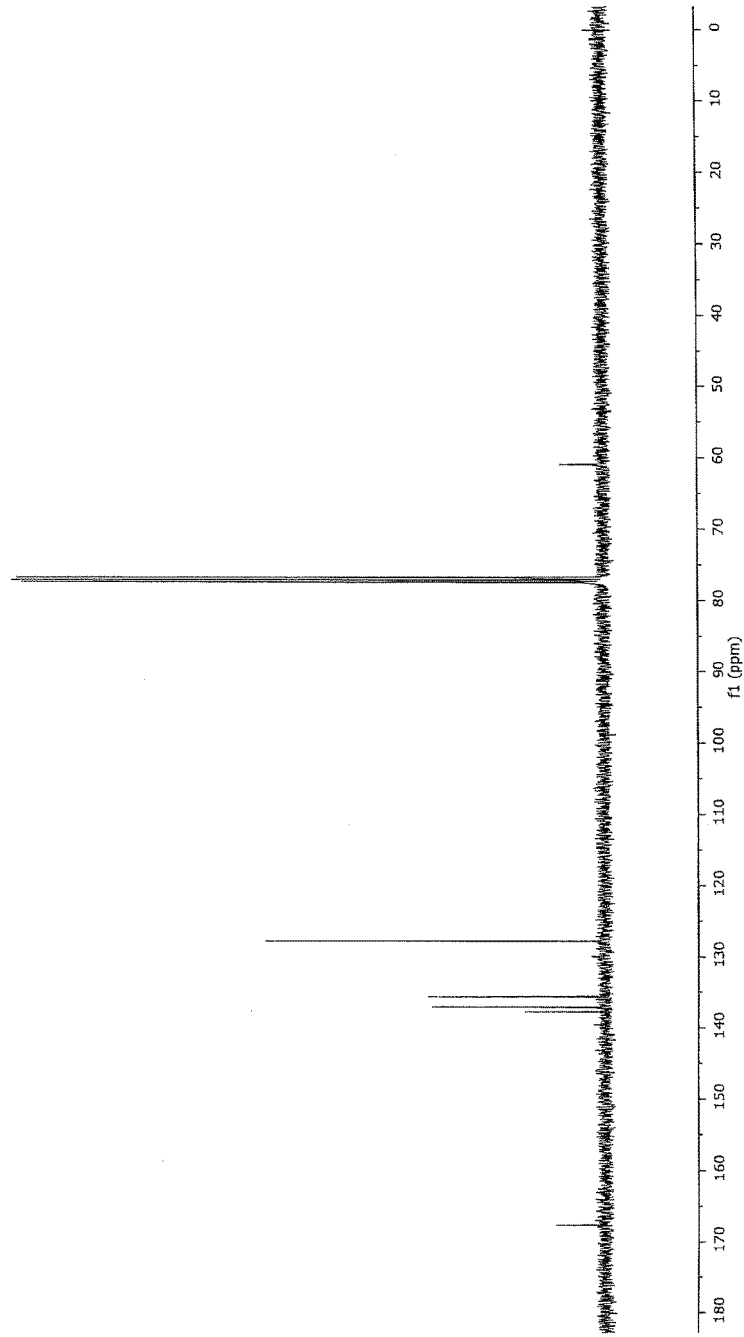

1,3-dichloro-5-((isocyanomethyl)sulfonyl)benzene (compound 3h) was prepared as follows. The sulfonyl formamide 2h was prepared from 3,5-dichlorobenzenesulfinate 411 (0.4 g, 1.77 mmol) following general method A with the modification of heating for 2 h at 90° C. Crude 2h was dehydrated following the general method with Et$_3$N to afford 249 mg (89%) of compound 3h as a white solid after purification by column chromatography using SiliaBond® Diol matrix (hexanes:Et$_2$O 70:30 as eluent): mp 82-83° C.; $^1$H NMR (400 MHz, Chloroform-d) δ 7.90 (d, J=1.9 Hz, 1H), 7.76 (t, J=1.9 Hz, 1H), 4.66 (s, 1H); $^{13}$C NMR (100 MHz, Chloroform-d) δ 167.66, 137.82, 137.13, 135.70, 127.81, 61.01; IR (ATR) 3079, 2145, 1570, 1344, 1161, 1135, 804, 666; HRMS calculated for C$_8$H$_6$FNO$_2$S, 287.9050. found 287.9052 (M+K)$^+$. An analogous reaction using procedure B gave 87% of compound 3h. See FIGS. 12 and 13.

Example 30

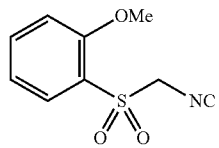

Figure 14:
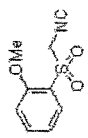
FIGS. 14 and 15 illustrate NMR data relating to the synthesis of 1-((isocyanomethyl)sulfonyl)-2-methoxybenzene, in accordance with certain embodiments of the invention.
Figure 14:
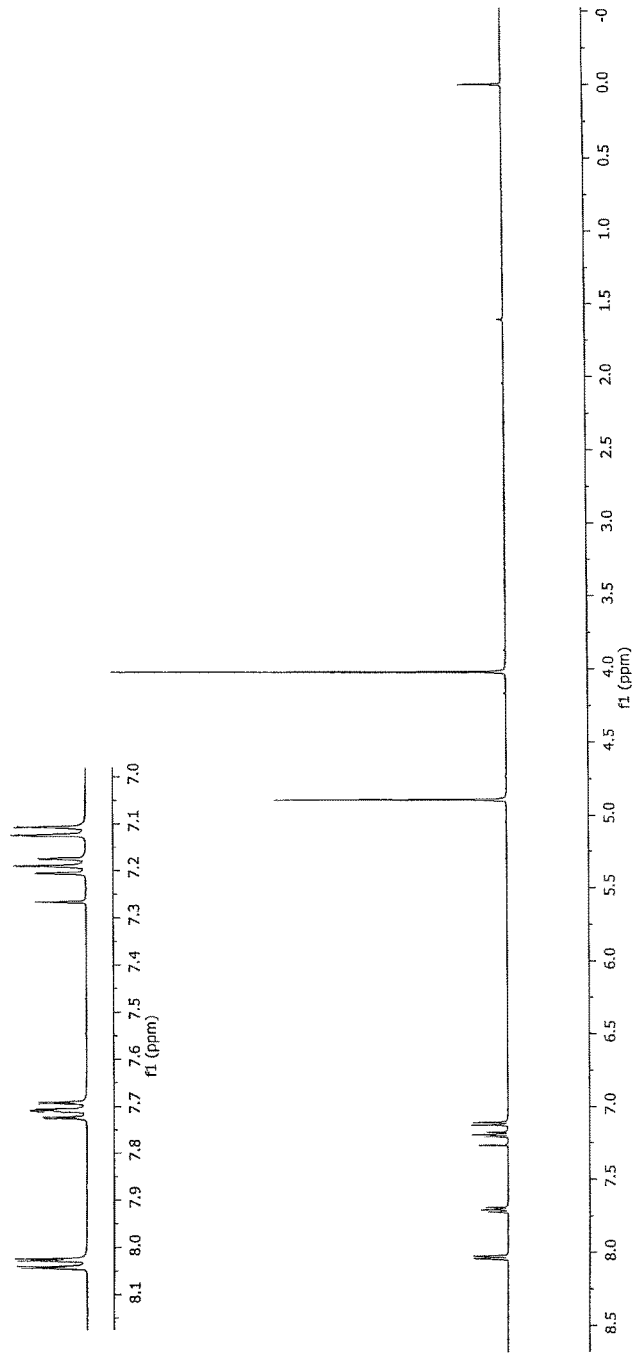
Figure 15:
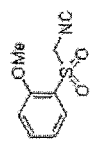
Figure 15:
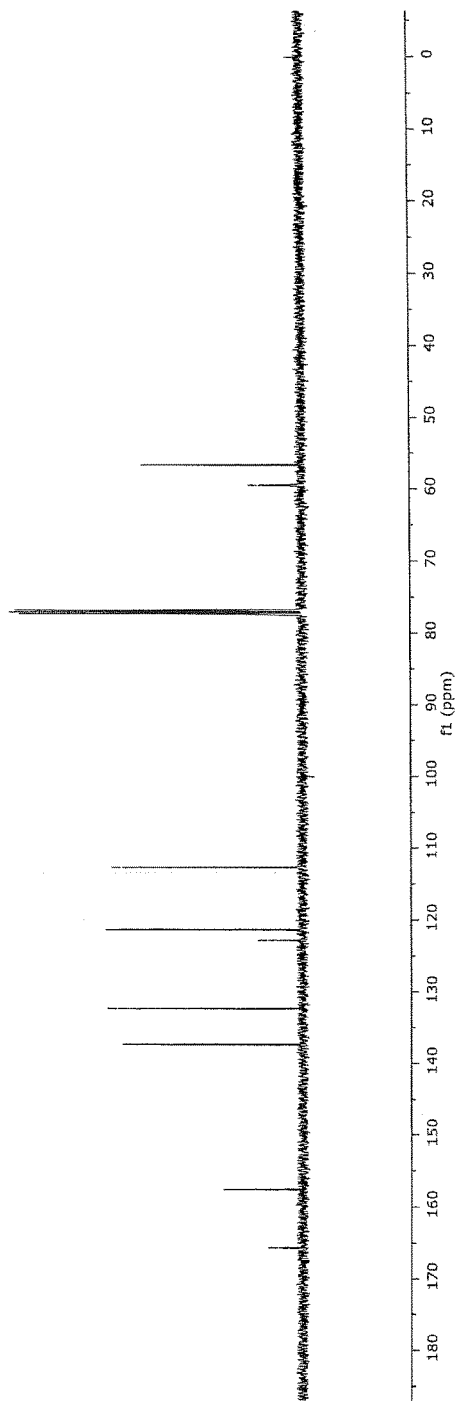

1-((Isocyanomethyl)sulfonyl)-2-methoxybenzene (compound 3i) was prepared as follows. The sulfonyl formamide 2i was prepared from methyl 2-methoxybenzenesulfinate 4i (2 g, 10.74 mmol) following general method B with the modification of heating for 2.5 h at 90° C. Crude 2i was dehydrated following the general method with i-Pr$_2$NH to afford 1.49 g (66%) of compound 3i as a slightly amber solid after purification on SiO$_2$ (radial chromatography, 4 mm rotor, hexanes:acetone gradient 80:20 to 40:60). The pure product exhibited spectral data identical to that exhibited from previously reported material: $^1$H NMR (500 MHz, Chloroform-d) δ 8.03 (dd, J=7.9, 1.8 Hz, 1H), 7.71 (ddd, J=8.4, 7.4, 1.8 Hz, 1H), 7.19 (td, J=7.7, 1.0 Hz, 1H), 7.12 (dd, J=8.4, 0.9 Hz, 1H), 4.89 (s, 2H), 4.02 (s, 3H); $^{13}$C NMR (125 MHz, Chloroform-d) δ 165.69, 157.60, 137.40, 132.32, 122.85, 121.37, 112.71, 59.51, 56.72. See FIGS. 14 and 15.

Example 31

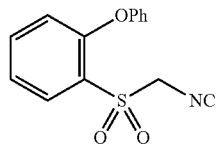

Figure 16:
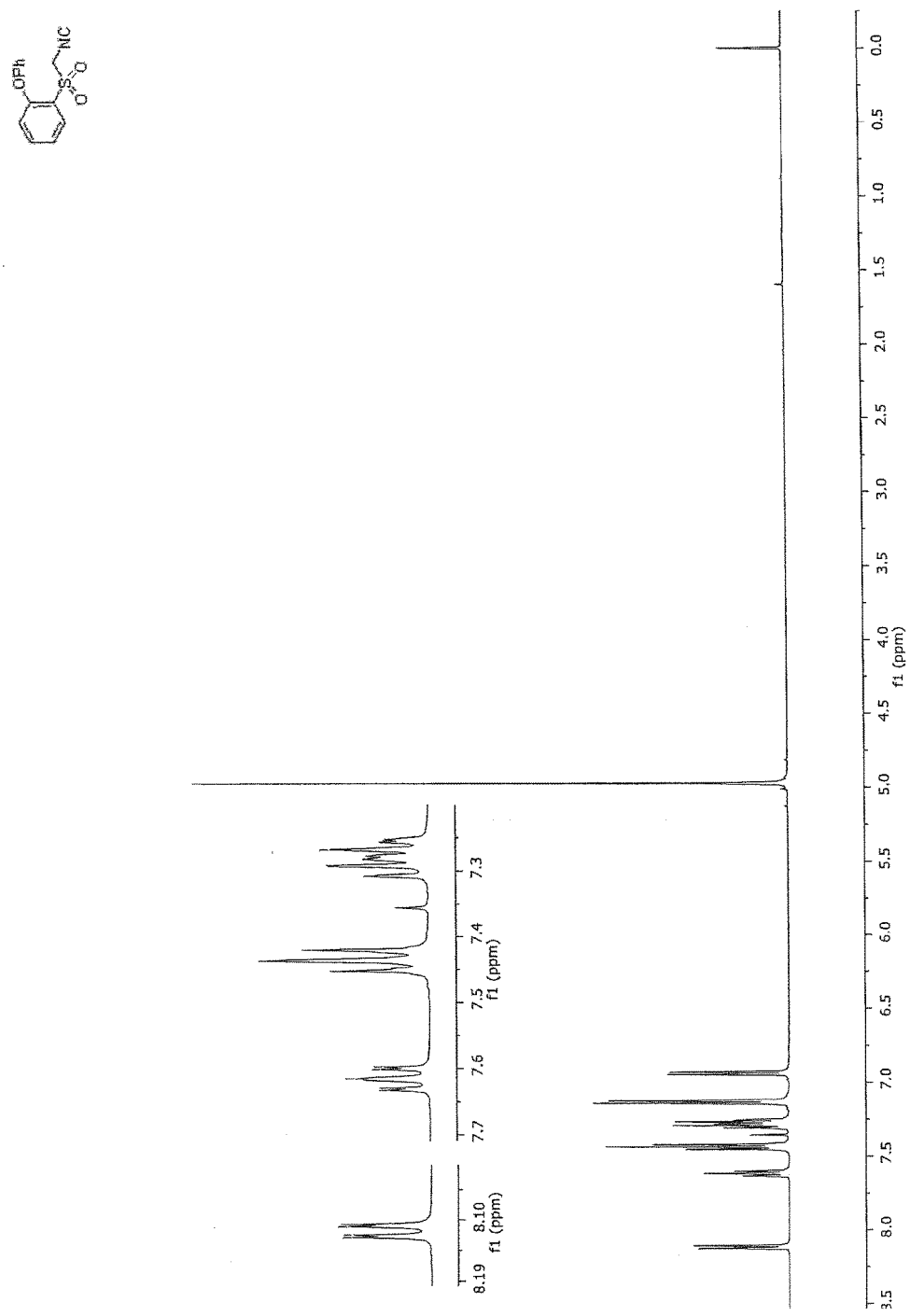
FIGS. 16 and 17 illustrate NMR data relating to the synthesis of 1-((isocyanoinethyl)sulfonyl)-2-phenoxybenzene, in accordance with certain embodiments of the invention.
Figure 17:
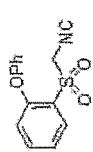
Figure 17:
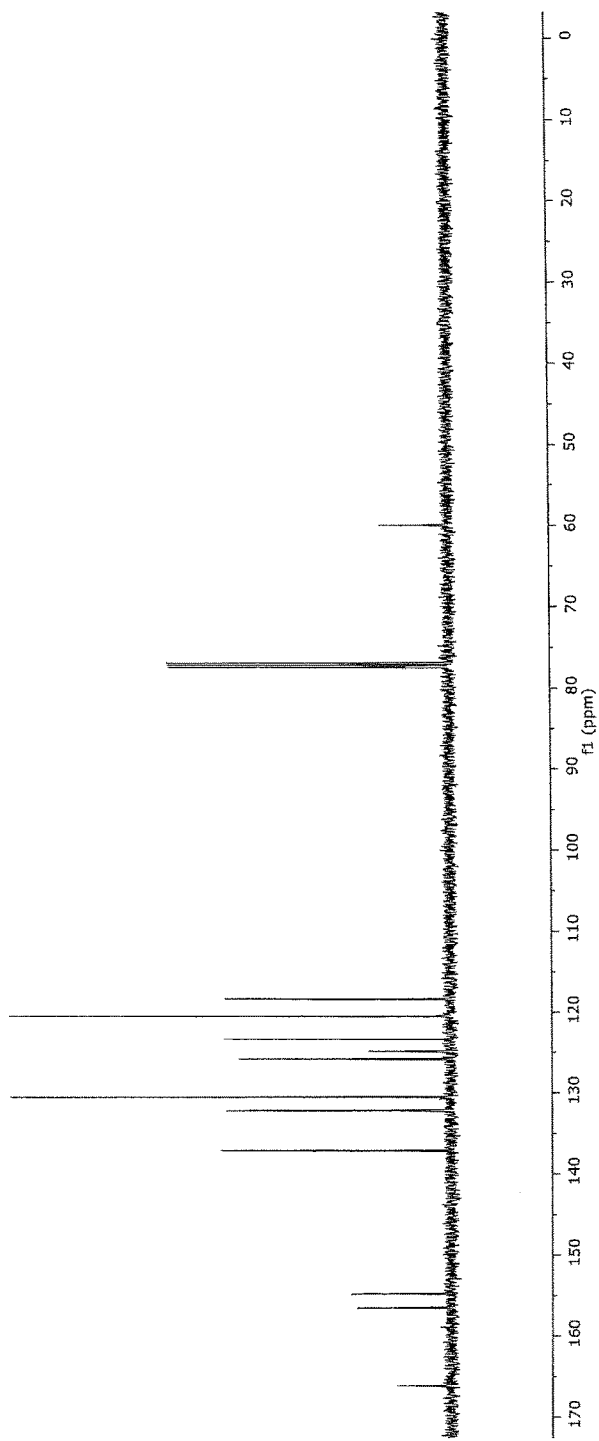

1-((Isocyanomethypsulfonyl)-2-phenoxybenzene (compound 3j) was prepared as follows. The sulfonyl formamide 2j was prepared from methyl 2-phenoxybenzenesulfinate 4j (1 g, 4 mmol) following general method A with the modification of heating for 2.5 h at 90° C. Crude 2j was dehydrated following the general method using i-Pr$_2$NH to afford 685 mg (71%) of compound 3j as a white solid after purification on SiO$_2$ (radial chromatography, 4 mm rotor, hexanes:EtOAc 70:30: mp 67-68° C.; $^1$H NMR (500 MHz, Chloroform-d) δ 8.12 (dd, J=7.9, 1.7 Hz, 1H), 7.62 (ddd, J=8.8, 7.4, 1.8 Hz, 1H), 7.47-7.40 (m, 2H), 7.32-7.24 (m, 2H), 7.13 (d, J=7.6 Hz, 2H), 6.94 (d, J=8.4 Hz, 1H), 4.97 (s, 2H); $^{13}$C NMR (125 MHz, Chloroform-d) δ 166.10, 156.45, 154.71, 137.07, 132.16, 130.51, 125.79, 124.81, 123.32, 120.41, 118.30, 59.95; IR (ATR) 3001, 2146, 1583, 1467, 1336, 1148, 749; HRMS calculated for $C_{14}H_{11}NO_3S$, 312.0091. found 312.0092 (M+K)$^+$. See FIGS. 16 and 17.

Example 32

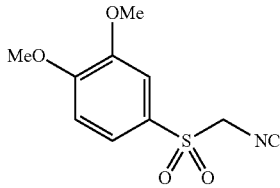

Figure 18:
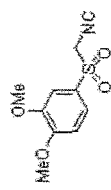
FIGS. 18 and 19 illustrates NMR data relating to the synthesis of 4-((isocyanomethypsulfonyl)-1,2-dimethoxybenzene, in accordance with certain embodiments of the invention.
Figure 18:
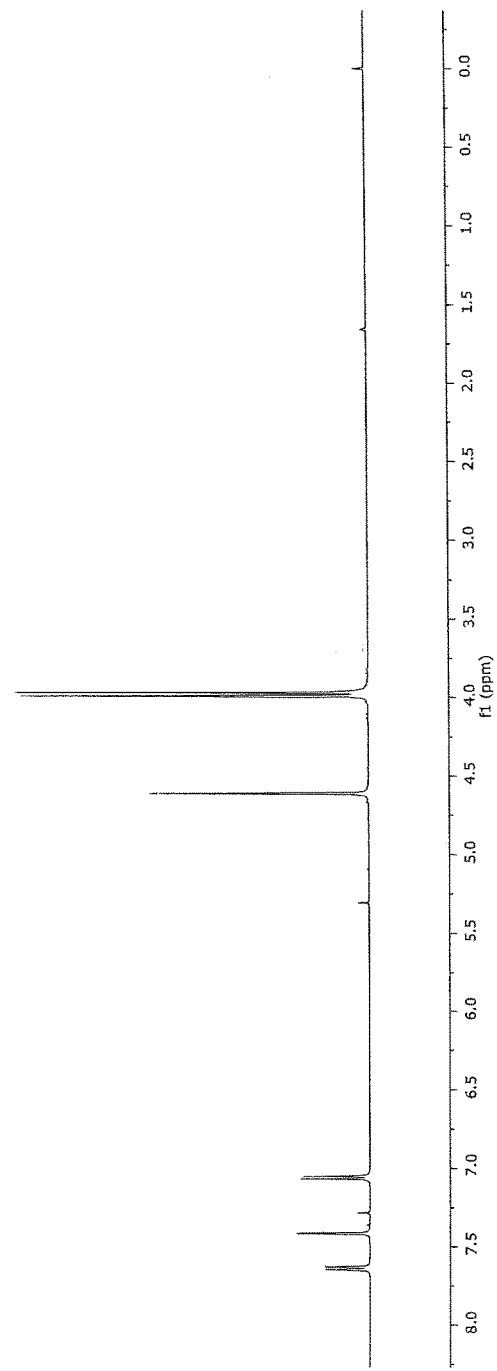
Figure 19:
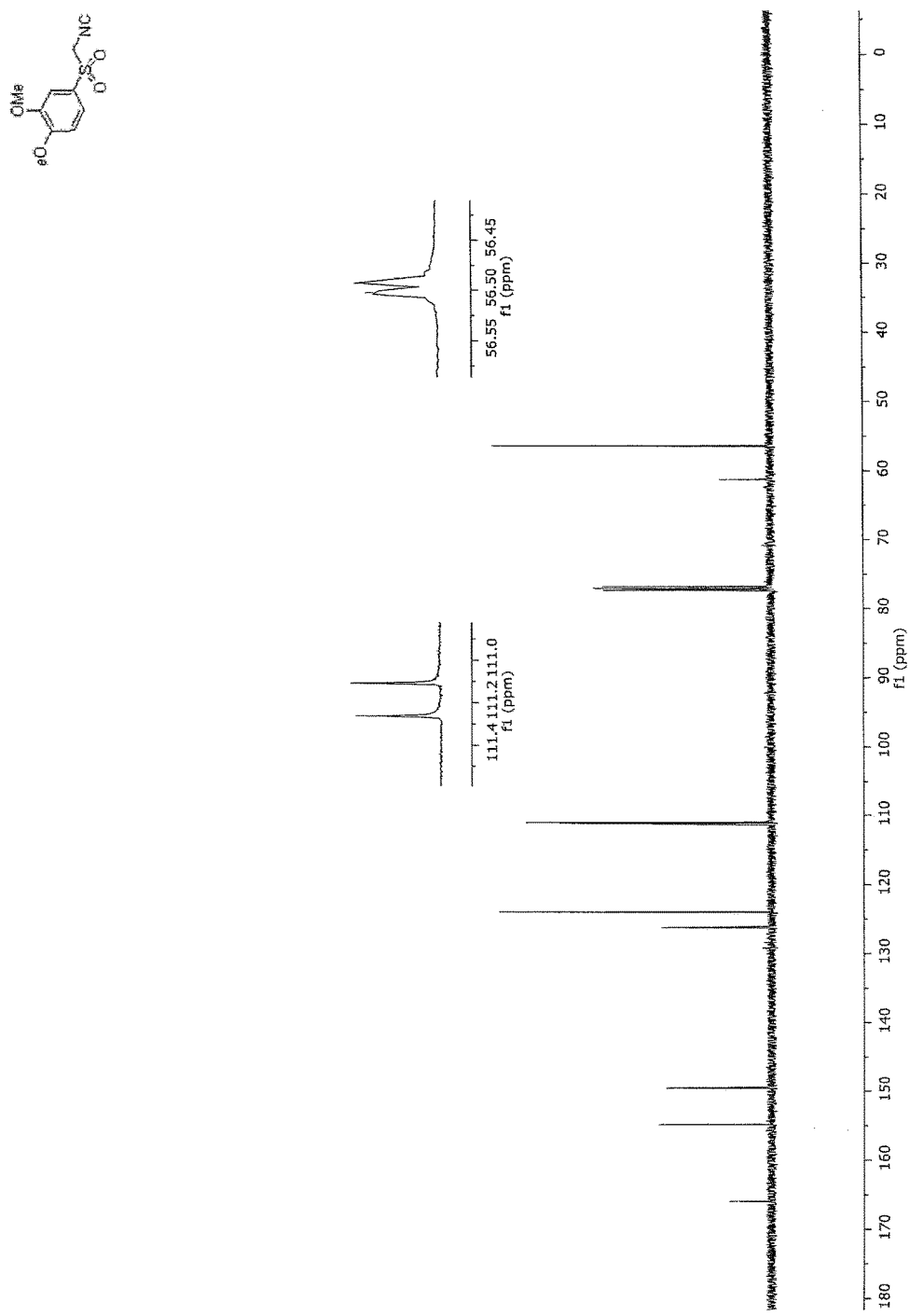

4-((isocyanomethyl)sulfonyl)-1,2-dimethoxybenzene (compound 3k) was prepared as follows. The sulfonyl formamide 2k was prepared from 3,4-dimethoxybenzenesulfinate 4k (200 mg, 0.925 mmol) following the general method A with the modification of heating for 2 h at 90° C. Crude 2k was dehydrated following the general method with i-Pr$_2$NH to afford 105 mg (45%) of compound 3k as a yellowish solid after purification on SiO$_2$ (flash chromatography using hexanes:Et$_2$O (80:20) as eluent): mp 101-102° C.; $^1$H NMR (500 MHz, Chloroform-d) δ 7.63 (dd, J=8.5, 2.2 Hz, 1H), 7.41 (d, J=2.2 Hz, 1H), 7.06 (d, J=8.5 Hz, 1H), 4.61 (s, 2H), 3.99 (s, 3H), 3.97 (s, 3H); $^{13}$C NMR (125 MHz, Chloroform-d) δ 165.88, 154.84, 149.56, 126.22, 124.01, 111.19, 111.04, 61.25, 56.43, 56.42; IR (ATR) 2937, 2147, 1508, 1262, 1133, 728 cm$^{-1}$; HRMS calculated for $C_{10}H_{11}NO_4S$, 264.0301. found 264.0329 (M+Na)$^+$. See FIGS. 18 and 19.

Example 33

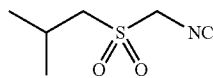

1-((isocyanomethyl)sulfonyl)-2-methylpropane (compound 3l) was prepared as follows. The sulfonyl formamide 2l was prepared from methyl 2-methylpropane-1-sulfinate 4l (500 mg, 3.67 mmol) following the general method B with the modification of heating for 3 h at 100° C. Crude 2l was dehydrated following the general method with i-Pr$_2$NH to afford 276 mg (45%) of compound 3l as a white solid after purification on SiO$_2$ (radial chromatography, 2 mm rotor, hexanes:Et$_2$O:dichloromethane 60:20:20): mp 59-60° C.; NMR (500 MHz, Chloroform-d) δ 4.54 (s, 2H), 3.13 (d, J=6.6 Hz, 2H), 2.43 (nontuplet, J=6.7 Hz, 1H), 1.19 (d, J=6.7 Hz, 6H); $^{13}$C NMR (125 MHz, Chloroform-d) δ 166.69, 59.24, 58.16, 23.74, 22.69; IR (ATR) 2970, 2147, 1319, 1136 cm$^{-1}$; HRMS calculated for $C_8H_{13}NO_2S$, 210.0559. found 210.0561 (M+Na)$^+$.

Example 34

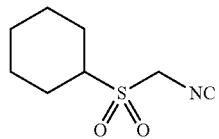

((Isocyanomethyl)sulfonyl)cyclohexane (compound 3m) was prepared as follows. The sulfonyl formamide 2m was prepared from methyl cyclohexansulfinate 4m (400 mg, 2.5 mmol) following general method A with the modification of adding three additional portions of paraformaldehyde, HCONH$_2$ and HCO$_2$H, at 2.5 h intervals with a total reaction time of 9 hours. Crude 2m was then dehydrated following the general method with i-Pr$_2$NH to afford 238 mg (51%) of compound 3m as a white solid after purification by filtration through a SiO$_2$ plug (hexanes:Et$_2$O 70:30 as eluent): mp. 73-74° C.; $^1$H NMR (400 MHz, Chloroform-d) δ 4.56 (s, 2H), 3.31 (tt, J=12.3, 3.7 Hz, 1H), 2.18 (d, J=12.8 Hz, 2H), 1.98 (d, J=11.7 Hz, 2H), 1.77 (d, J=11.8 Hz, 1H), 1.63 (qd, J=12.6, 3.8 Hz, 2H), 1.38 (qt, J=12.6, 3.4 Hz, 2H), 1.26 (qt, J=12.8, 3.2 Hz, 1H); $^{13}$C NMR (100 MHz, Chloroform-d) δ 166.53, 59.77, 55.56, 24.88, 24.86; IR (ATR) 2933, 2148, 1320, 1129, 906, 732 cm$^{-1}$; HRMS calculated for $C_6H_{11}NO_2S$, 184.0403. found 184.0383 (M+Na)$^+$.

Example 35

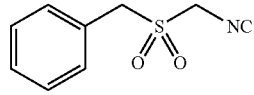

((Isocyanomethyl)sulfonyl)methyl)benzene (compound 3n) was prepared as as follows. The sulfonyl formamide 2n was prepared from methyl phenylmethanesulfinate 4n (0.5 g, 2.94 mmol) following the general method A with the modification of heating for 2.5 h at 90° C. Crude 2n was dehydrated following the general dehydration method with i-Pr$_2$NH to afford 324 mg (57%) of compound 3n as a white solid after purification on SiO$_2$ (radial chromatography, 2 mm rotor, hexanes:Et$_2$O 70:30 then hexanes:Et$_2$O:acetone 40:30:30): mp 105-106° C. (lit. 103-106° C.); NMR (500 MHz, Chloroform-d) δ 7.46 (s, 5H), 4.49 (s, 2H) (lit. 4.50), 4.31 (s, 2H); $^{13}$C NMR (125 MHz, Chloroform-d) δ 166.99, 130.74, 129.97, 129.65, 126.29, 57.07, 55.62. IR (ATR) 3007, 2141, 1303, 1133 cm$^{-1}$; HRMS calculated for $C_9H_9NO_2S$, 233.9986. found 233.9988 (M+Kr.

General Oxidation Method of Formamides

Solid m-CPBA (2.2 equiv) was added to a 0° C., dichloromethane solution (0.5 M) of the crude sulfanyl formamide (1 eq) in three portions at 10 min intervals. After 2.5 h, the reaction was diluted with cold, saturated NaHCO$_3$, the phases were separated and the aqueous phase was then extracted with dichloromethane (×5). The combined organic extract was washed with 0° C., saturated aqueous NaHCO$_3$ and then with 0° C., 5% aqueous Na$_2$SO$_3$. The aqueous layer was re-extracted once with dichloromethane. The organic extract was dried (Na$_2$SO$_4$) and concentrated to afford the crude sulfonyl formamide (a-z) that was sufficiently pure to use in the following dehydration.

Example 36

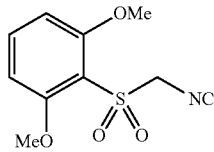

Figure 20:
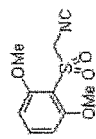
FIGS. 20 and 21 illustrate NMR data relating to the synthesis of 2-((isocyanomethyl)sulfonyl)-1,3-dimethoxybenzene, in accordance with certain embodiments of the invention.
Figure 20:
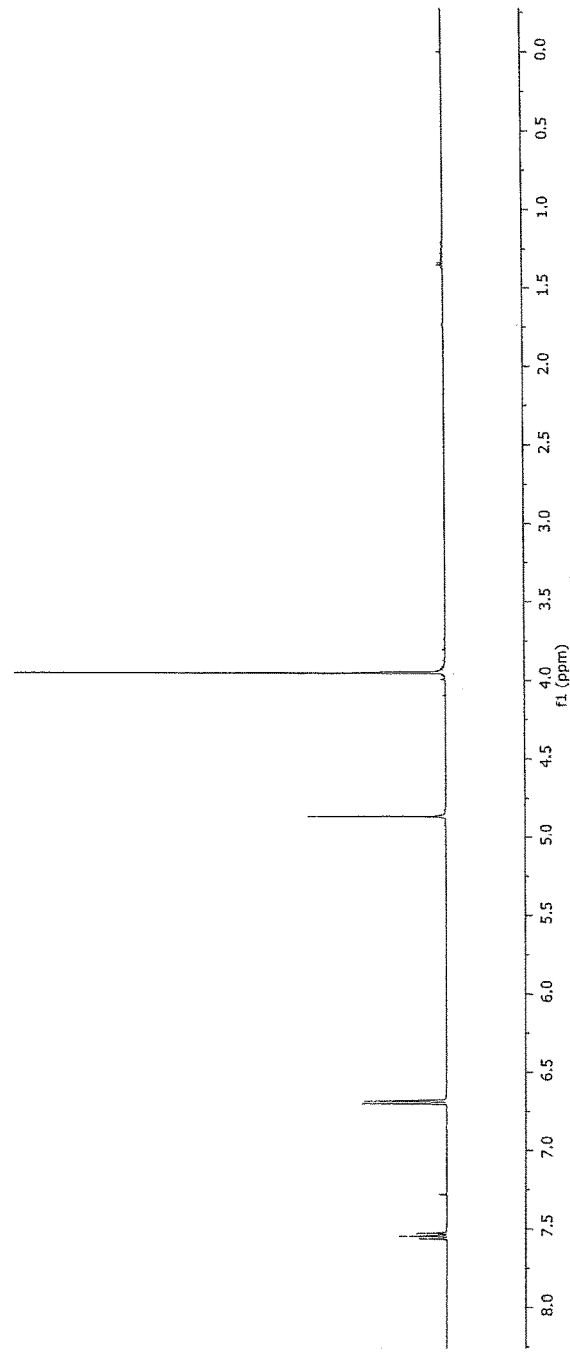
Figure 21:
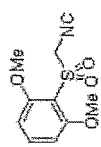
Figure 21:
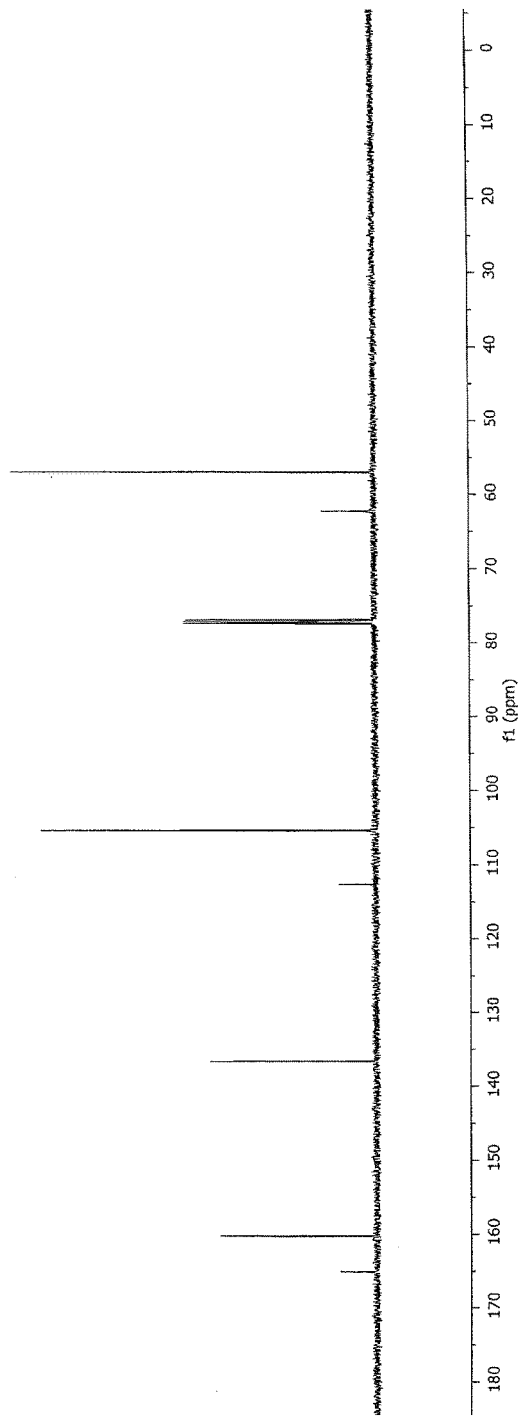

2-((Isocyanomethyl)sulfonyl)-1,3-dimethoxybenzene (compound 3p) was prepared as follows. The sulfanyl formamide 12p was prepared from 2,6-dimethoxybenzenethiol 11p (1 g, 5.88 mmol) following general method A with the modification of heating for 3 h at 100° C. Crude 12p was filtered through a plug of Florisil (toluene/EtOAc 70:30 as eluant) to afford 1.3 g of sulfanyl formamide 12p after removal of the volatiles. For the major rotamer: $^1$H NMR (500 MHz, Chloroform-d) δ 8.07 (d, J=1.6 Hz, 1H), 7.29 (t, J=8.4 Hz, 1H), 6.60 (d, J=8.4 Hz, 2H), 4.59 (d, J=6.0 Hz, 2H), 3.90 (s, 6H). Oxidation of 12p (1.3 g, 5.72 mmol) following the general m-CPBA method afforded 1.154 g of 13p as a white solid: $^1$H NMR (500 MHz, Chloroform-d) δ 8.10 (d, J=1.2 Hz, 1H), 7.47 (t, J=8.5 Hz, 1H), 7.01 (bs, 1H), 6.63 (d, J=8.5 Hz, 2H), 4.98 (d, J=6.9 Hz, 2H), 3.94 (s, 6H). After drying 13p (1.154 g, 4.45 mmol) under vacuum (ca. 2 h), the formamide was dehydrated following the general method using i-Pr$_2$NH to afford 572 mg (40%, 3 steps) of compound 3p as a white solid after purification on SiO$_2$ (radial chromatography, 2 mm rotor, using a hexanes:dichloromethane:acetone gradient 80:10:10 to 60:20:20): mp 90-91° C.; $^1$H NMR (500 MHz, Chloroform-d) δ 7.55 (t, J=8.5 Hz, 1H), 6.69 (d, J=8.5 Hz, 2H), 4.87 (s, 2H), 3.95 (s, 6H); $^{13}$C NMR (125 MHz, Chloroform-d) δ 165.08, 160.22, 136.66, 112.65, 105.41, 62.29, 56.99; IR (ATR) 2944, 2148, 1582, 1476, 1331, 1253, 1146, 1099, 779 cm$^{-1}$; HRMS calculated for C$_{10}$H$_{11}$NO$_4$S, 280.0040. found 280.0061 (M+K)$^+$. See FIGS. 20 and 21.

Example 37

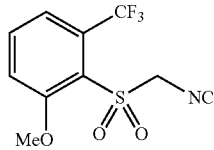

Figure 22:
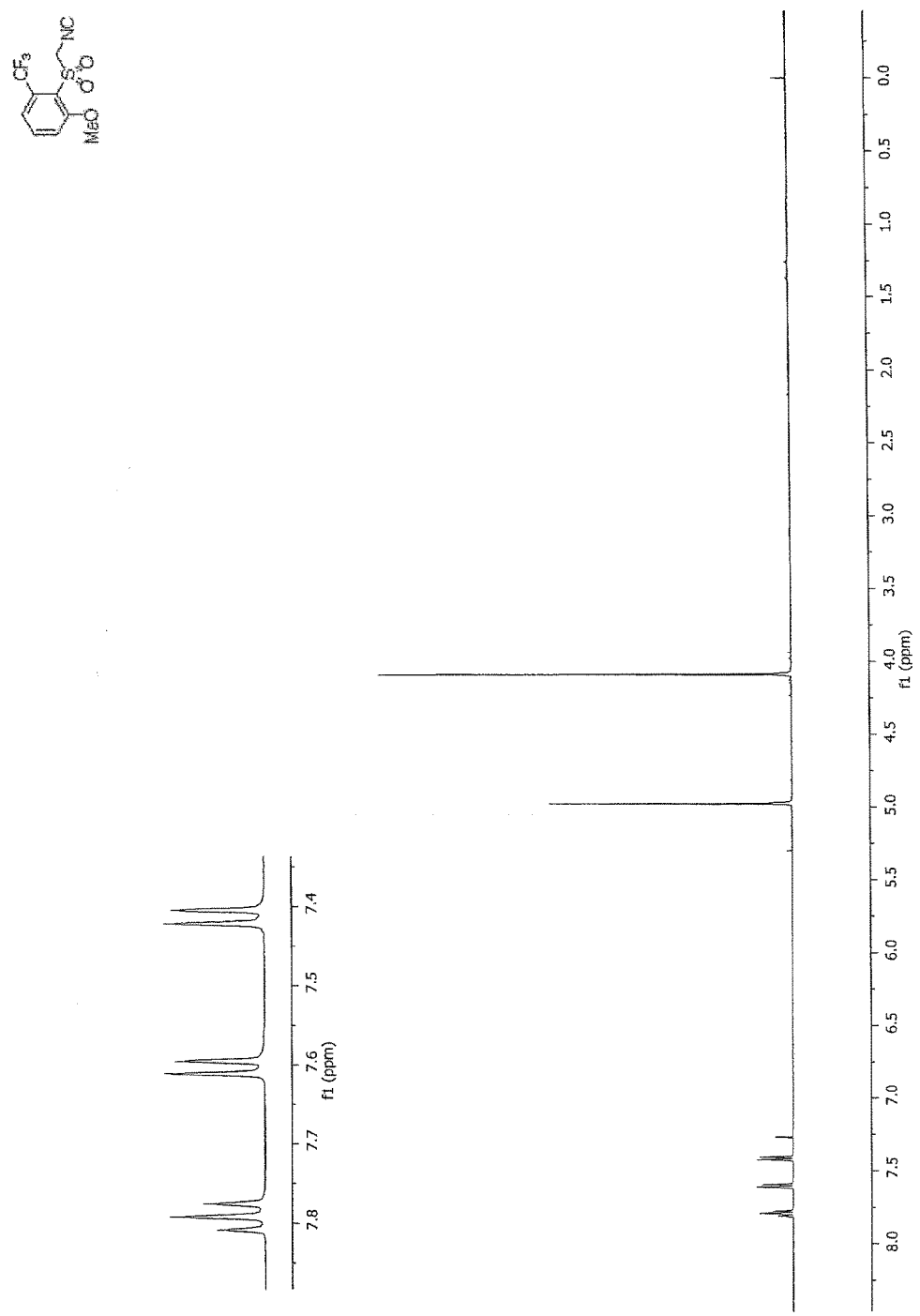
FIGS. 22 and 23 illustrate NMR data relating to the synthesis of 2-((isocyanomethyl)sulfonyl)-1-methoxy-3-(trifluoromethyl)benzene, in accordance with certain embodiments of the invention.
Figure 23:
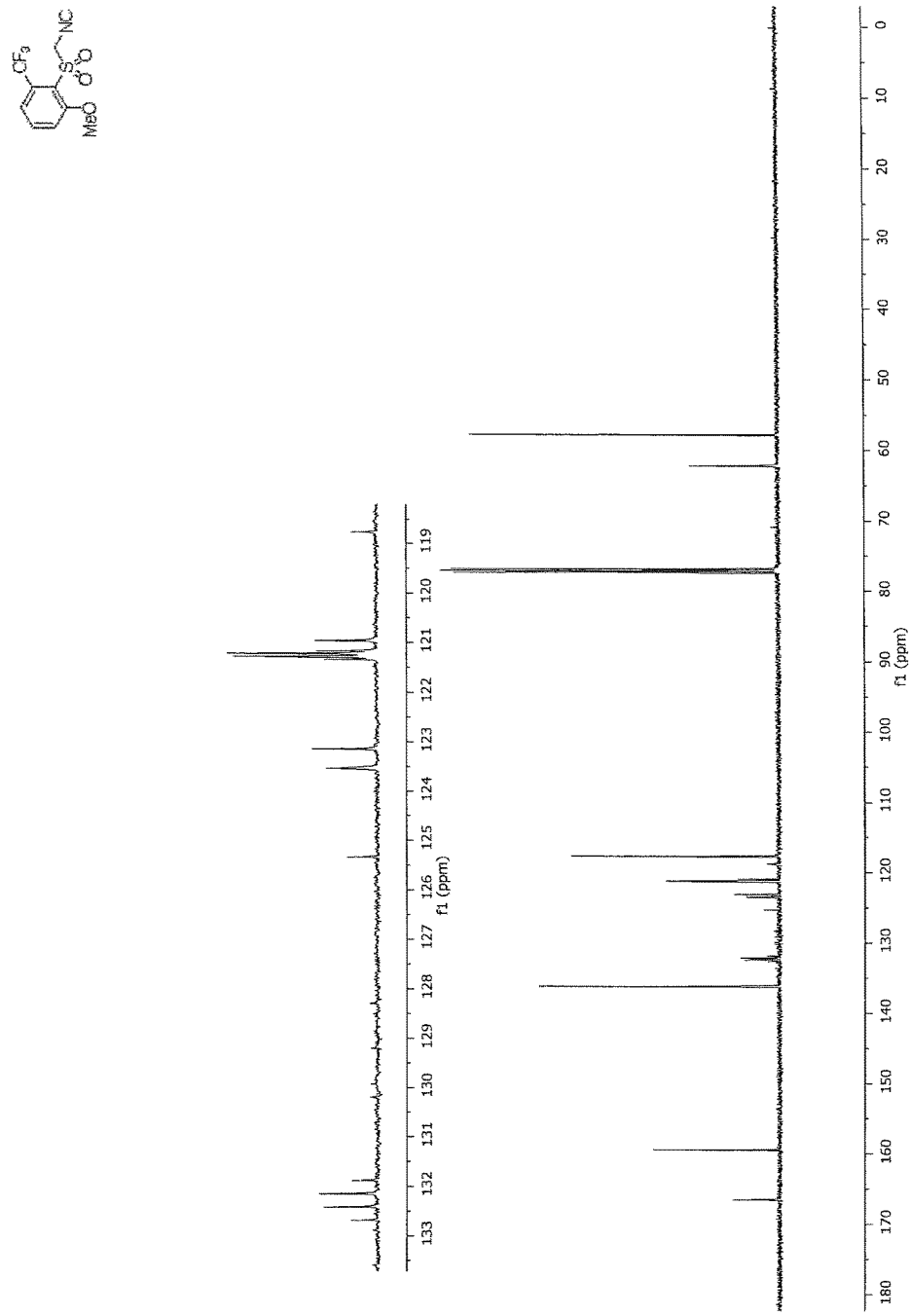

3p 2-((Isocyanomethypsulfonyl)-1-methoxy-3-(trifluoromethyl)benzene (compound 3q) was prepared as follows. The sulfanyl formamide 12q was prepared from 2-methoxy-6-(trifluoromethyl)benzenethiol 11q (1 g, 4.8 mmol) following the general method A with the modification of heating for 2 h at 90° C. and then, after allowing the reaction to cool, adding cold water (0° C., 10 mL). Crude 12q was filtered and then left in a freezer (−30° C.) for 15 min. The slightly pink solid was washed with copious cold water, cold hexanes (5 mL), and refiltered. The solid was then washed with cold hexanes/Et$_2$O (50:50, 10 mL) and dried under vacuum for 2 h to afford 1.083 g of formamide as a solid. $^1$H NMR for the major rotamer: $^1$H NMR (500 MHz, Chloroform-d) δ 8.02 (s, 1H), 7.44 (t, J=8.1 Hz, 1H), 7.34 (d, J=7.9 Hz, 1H), 7.13 (d, J=8.0 Hz, 1H), 5.87 (bs, 1H), 4.72 (d, J=6.4 Hz, 2H), 4.00 (s, 3H). Formamide 12q (220 mg, 8.29 mmol) was oxidized to the sulfonyl formamide 13q following the general m-CPBA method with the modification of performing the reaction for 3 h at rt until complete conversion was determined as judged by $^1$H NMR: $^1$H NMR (500 MHz, Chloroform-d) δ 8.01 (s, 1H), 7.69 (t, J=8.2 Hz, 1H), 7.49 (d, J=7.9 Hz, 1H), 7.35 (d, J=8.6 Hz, 1H), 6.76 (s, 1H), 5.06 (d, J=7.0 Hz, 2H), 4.14 (s, 3H). After drying under vacuum (ca. 2 h), the crude 13q was dehydrated following the general method with Et$_3$N to afford 124 mg (46%, 3 steps) of compound 3q as a slightly yellow solid after purification on SiO$_2$ (column chromatography, hexanes:EtOAc 80:20 to 70:30): mp 84-85° C.; $^1$H NMR (500 MHz, Chloroform-d) δ 7.79 (t, J=8.1 Hz, 1H), 7.60 (d, J=8.0 Hz, 1H), 7.41 (d, J=8.6 Hz, 1H), 4.97 (s, 3H), 4.09 (s, 3H); $^{13}$C NMR (125 MHz, Chloroform-d) δ 166.57, 159.47, 136.23, 132.29 (q, J=33.5 Hz), 123.54, 122.06 (q, J=274.9 Hz), 121.26 (q, J=7.4 Hz), 117.73, 62.21, 57.83. IR (ATR) 2947, 2148, 1587, 1349, 1305, 1142, 1099, 1022, 800 cm$^{-1}$; HRMS calculated for C$_{10}$H$_8$F$_3$NO$_3$S, 317.9809. found 317.9816 (M+K)$^+$. See FIGS. 22 and 23.

Example 38

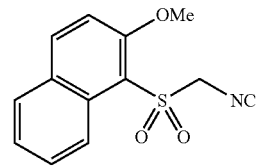

3r 2-((isocyanomethypsulfonyl)-3-methoxynaphthalene (compound 3r) was prepared as follows. The sulfanyl formamide 12r was prepared from 2-methoxynaphtalene-1-thiol 11r (1.5 g, 7.89 mmol) following the general method A with the modification of heating for 3 h at 105° C. Crude 12r was recrystallized from benzene/hexanes and filtered to yield 1.53 g crystalline material. $^1$H NMR for major rotamer: $^1$H NMR (500 MHz, Chloroform-d) δ 8.57 (d, J=8.7 Hz, 1H), 7.99 (d, J=1.5 Hz, 1H), 7.90 (d, J=9.1 Hz, 1H), 7.79 (d, J=8.2 Hz, 1H), 7.55 (ddd, J=8.6, 7.0, 1.4 Hz, 1H), 7.39 (ddd, J=8.1, 6.8, 1.2 Hz, 1H), 7.32 (d, J=9.0 Hz, 1H), 6.22 (bs, 1H), 4.66 (d, J=6.3 Hz, 2H), 4.07 (s, 3H). Sulfanyl formamide 12r (1.53 g, 6.19 mmol) was oxidized to the sulfonyl formamide 13r following the general m-CPBA method to afford, after removal of volatiles, 1.85 g of 13r as a white solid: $^1$H NMR (500 MHz, Chloroform-d) δ 9.27 (d, J=9.2 Hz, 1H) 8.09 (d, J=9.3 Hz, 1H), 7.93 (d, J=1.2 Hz, 1H), 7.80 (dd, J=8.2, 1.5 Hz, 1H), 7.60 (ddd, J=8.7, 6.8, 1.6 Hz, 1H), 7.44 (ddd, J=8.0, 6.8, 1.1 Hz, 1H), 7.34 (d, J=9.1 Hz, 1H), 6.38 (bs, 1H), 5.09 (d, J=6.9 Hz, 2H), 4.19 (s, 3H). After drying 13r under vacuum (ca. 2 h), the crude sulfonyl formamide (1 g, 3.58 mmol) was dehydrated following the general method with i-Pr$_2$NH to afford 850 mg (56%, 3 steps) of compound 3r as a slightly yellow solid after purification on SiO$_2$ (radial chromatography, 4 mm rotor, hexanes:dichloromethane:acetone 40:30:30): mp 100-102° C. (dec); $^1$H NMR (500 MHz, Chloroform-d) δ 9.24 (dq, J=9.0, 0.9 Hz, 1H), 8.14 (d, J=9.1 Hz, 1H). 7.82 (d, J=8.1 Hz, 1H), 7.66 (ddd, J=9.0, 6.9, 1.5 Hz, 1H), 7.47 (ddd, J=8.0, 6.9, 1.1 Hz, 1H), 7.34 (d, J=9.1 Hz, 1H), 4.98 (s, 2H), 4.12 (s, 3H); $^{13}$C NMR (125 MHz, Chloroform-d) δ 165.56, 159.05, 138.71, 132.16, 130.01, 129.41, 128.99, 125.36, 123.42, 116.56, 113.05, 62.03, 57.89; IR (ATR) 2990, 2144, 1597, 1509, 1338, 1331, 1142, 908, 815, 730 cm$^{-1}$; HRMS calculated for $C_{13}H_{11}NO_3S$, 284.0352. found 284.0353 (M+Na)$^+$.

Example 39

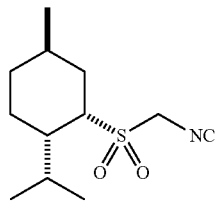

(1R,2S,4R)-2-((isocyanomethyl)sulfonyl)-4-isopropyl-1-methylcyclohexane (compound 3s) was prepared as follows. The sulfanyl formamide 12s was prepared from neomenthyl thiol (0.2 g, 1.16 mmol) according to the general method A with the modification of heating for 3 h at 110° C. Crude 12s was filtered through a florisil plug (toluene/EtOAc 90:10 as eluent) to obtaining 0.18 g of partially purified material. $^1$H NMR for the major rotamer: $^1$H NMR (500 MHz, Chloroform-d) δ 8.21 (s, 1H), 5.81 (bs, 1H), 4.60 (dd, J=14.1, 7.3 Hz, 1H), 4.22 (dd, J=14.1, 5.3 Hz, 1H), 3.28 (m, 1H), 2.04-1.94 (m, 1H), 1.94-1.82 (m, 2H), 1.75-1.69 (m, 1H), 1.65-1.53 (m, 1H), 1.25 (ddd, =13.7, 11.8, 3.1 Hz, 1H), 1.13-1.00 (m, 3H), 0.93 (d, J=6.6 Hz, 3H), 0.90 (d, J=3.3 Hz, 3H), 0.89 (d, J=3.2 Hz, 3H). Sulfanyl formamide 12s (0.18 g, 78.5 mmol) was oxidized to the sulfonyl formamide 13s following the general m-CPBA method to afford 0.25 g of compound 13s as a semisolid: $^1$H NMR (500 MHz, Chloroform-d) δ 8.28 (s, 1H), 6.70 (s, 2H), 4.90 (dd, J=14.4, 7.6 Hz, 2H), 4.25 (dd, J=14.4, 5.9 Hz, 2H), 3.54 (bs, 1H), 2.32 (d, 1H), 2.23-2.07 (m, 1H), 1.95-1.84 (m, 1H), 1.84-1.70 (m, 2H), 1.04 (d, J=6.4 Hz, 3H), 0.97-0.92 (m, 1H), 0.95 (d, J=6.4 Hz, 3H), 0.90 (d, J=6.5 Hz, 3H). After drying under vacuum (ca. 2 h), crude 13s (250 mg, 1.09 mmol) was dehydrated following the general method with i-Pr$_2$NH to afford 154 mg (55%, 3 steps) of compound 3s as a colorless oil after purification on SiO$_2$ (radial chromatography, 1 mm rotor, hexanes:EtOAc 90:10). An analytically pure sample was obtained by crystallization from pentane: mp 62-63° C., [α]$_D$ +40.2° (lit. 68° C. and [α]$_D$+42.7° respectively); IR (ATR) 2954, 2143, 1328, 1127 cm$^{-1}$; $^1$H NMR (500 MHz, Chloroform-d) δ 4.59 (d, J=15.4 Hz, 1H), 4.39 (d, J=15.4 Hz, 1H), 3.94-3.87 (m, 1H), 2.25 (ddt, J=15.0, 3.3, 2.4 Hz, 1H), 2.13-2.01 (m, 2H), 1.96-1.86 (m, 1H), 1.86-1.80 (m, 2H), 1.47-1.37 (m, 2H), 1.10 (d, J=6.5 Hz, 3H), 1.03-0.95 (m, 1H), 0.97 (d, J=6.5 Hz, 3H), 0.93 (d, J=6.5 Hz, 3H); $^{13}$C NMR (125 MHz, Chloroform-d) δ 166.42, 59.60, 59.00, 49.33, 36.57, 34.98, 29.67, 26.78, 24.94, 22.29, 21.95, 21.80. HRMS calculated for $C_{12}H_{21}NO_2S$, 266.1185. found 266.1185 (M+Na)$^+$.

Example 40

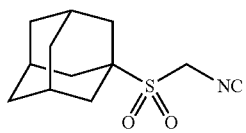

1-((Isocyanomethyl)sulfonyl)adamantane (compound 3t) was prepared as follows. The sulfanyl formamide 12t was prepared from 1-adamantanethiol following a modification of general method A: A toluene:formamide (1:6) solution (0.6 mL) of 1-adamantanethiol (300 mg, 1.78 mmol) was slowly added to the formic acid-formaldehyde solution over a 3 h period through the assistance of a syringe pump. 0.5 h after the addition, the reaction was worked up as described in general method A. Crude 12t was filtered through a florisil column (hexanes:EtOAc 60:40 as eluent) to afford 252 mg of partially purified 12t. $^1$H NMR for the major rotamer: $^1$H NMR (400 MHz, Chloroform-d) δ 8.12 (s, 1H), 5.67 (bs, 1H), 4.44 (d, J=5.7 Hz, 2H), 2.06 (bs, 3H), 1.96-1.82 (m, 6H), 1.76-1.65 (m, 6H). Sulfanyl formamide 12t (200 mg, 0.89 mmol) was oxidized to the sulfonyl formamide 13t following the general m-CPBA method to afford 217 mg of compound 13t as a solid: $^1$H NMR (400 MHz, Chloroform-d) δ 8.22 (s, 1H), 7.28 (bs, 1H), 4.68 (d, J=6.7 Hz, 2H), 2.18 (bs, 3H), 2.12-2.05 (m, 6H), 1.82-1.67 (m, 6H). After drying under vacuum (ca. 2 h), crude compound 13t (217, 0.84 mmol) was dehydrated following the general method with i-Pr$_2$NH to afford 106 mg (32%, 3 steps) of compound 3p as a white solid after purification on SiO$_2$ (flash chromatography, hexanes:EtOAc 75:25): mp 110-111° C.; $^1$H NMR (500 MHz, Chloroform-d) δ 4.58 (s, 1H), 2.24 (s, 2H), 2.14 (d, J=3.0 Hz, 4H), 1.77 (q, J=12.6 Hz, 5H); $^{13}$C NMR (125 MHz, Chloroform-d) δ 166.56, 64.60, 53.01, 35.51, 35.24, 28.14; IR (ATR) 2918, 2857, 2146, 1455, 1297, 1142 cm$^{-1}$. HRMS calculated for $C_{12}H_{17}NO_2S$, 278.0612. found 278.0639 (M+K)$^+$.

We claim:

1. An isonitrile of a general structure of Formula II:

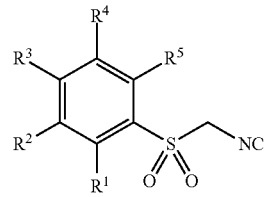

(II)

wherein $R^1$, $R^3$ and $R^5$ are each hydrogen and, $R^2$ and $R^4$ are the same and are each selected from halogen excluding Cl, and O—X wherein X is selected from alkyl and aryl.

2. An isonitrile of a general structure of Formula III:

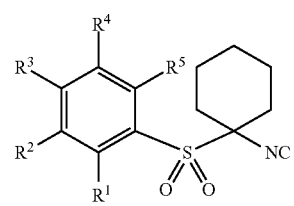

(III)

wherein $R^1$, $R^2$, $R^3$, $R^4$, and $R^5$ are the same or different and each is hydrogen, or wherein, one of $R^1$, $R^2$, $R^3$, $R^4$ and $R^5$ is selected from halogen, alkyl, haloalkyl and O—X wherein X is selected from alkyl and aryl, and each remaining $R^1$, $R^2$, $R^3$, $R^4$ and $R^5$ substituent is hydrogen.

3. A method of preparing an arylsulfonyl isonitrile represented by a general structure of Formula II:

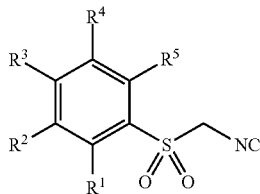

(II)

wherein, $R^1$, $R^2$, $R^3$, $R^4$ and $R^5$ are the same and each is hydrogen, or wherein, one of $R^1$, $R^2$, $R^3$, $R^4$ and $R^5$ is alkyl and each remaining $R^1$, $R^2$, $R^3$, $R^4$ and $R^5$ substituent is hydrogen, or wherein, one of $R^1$, $R^2$, $R^3$, $R^4$ and $R^5$ is selected from F, Cl, $CF_3$ and $CCl_3$, and each remaining $R^1$, $R^2$, $R^3$, $R^4$ and $R^5$ substituent is hydrogen, or wherein, two of $R^1$, $R^2$, $R^3$, $R^4$ and $R^5$ are OX, wherein X is selected from alkyl and aryl, and each remaining $R^1$, $R^2$, $R^3$, $R^4$ and $R^5$ substituent is hydrogen, or wherein, one of $R^1$, $R^2$, $R^3$, $R^4$ and $R^5$ is OX, wherein X is aryl, and each remaining $R^1$, $R^2$, $R^3$, $R^4$ and $R^5$ substituent is hydrogen, or wherein, one of $R^1$, $R^2$, $R^3$, $R^4$ and $R^5$ is OX, wherein X is selected from alkyl and aryl, one of $R^1$, $R^2$, $R^3$, $R^4$ and $R^5$ is selected from halogen and haloalkyl, and each remaining $R^1$, $R^2$, $R^3$, $R^4$ and $R^5$ substituent is hydrogen, or wherein, each of $R^2$ and $R^4$ is the same or different and is selected from halogen and haloalkyl, and each of $R^1$, $R^3$ and $R^5$ is hydrogen, wherein $R^1$ and $R^2$, or $R^2$ and $R^3$, or $R^3$ and $R^4$, or $R^4$ and $R^5$ together form a benzo ring, which forms a naphthalyl group, comprising:
reacting an arylsulfinate of the below Formula V with formamide to form an intermediate formamide-containing material of the below Formula VI; and
dehydrating the intermediate formamide-containing material of the below Formula VI to form the arylsulfonyl isonitrile of the Formula II:

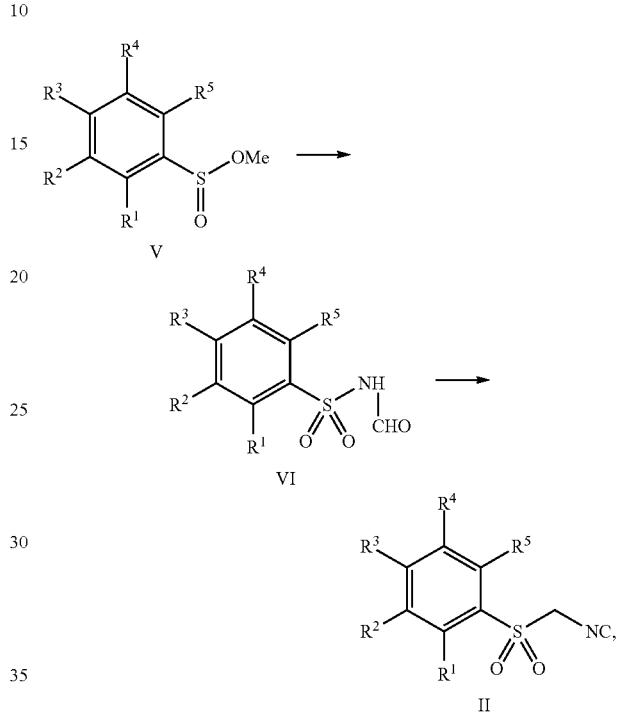

* * * * *